United States Patent
Tucker et al.

(10) Patent No.: US 7,846,451 B2
(45) Date of Patent: *Dec. 7, 2010

(54) *MORAXELLA CATARRHALIS* PROTEIN, NUCLEIC ACID SEQUENCE AND USES THEREOF

(75) Inventors: Kenneth Tucker, Frederick, MD (US); Ulrich F. Tillman, Mount Laurel, NJ (US)

(73) Assignee: Emergent Product Development Gaithersburg, Inc., Gaithersburg, MD (US)

( * ) Notice: Subject to any disclaimer, the term of this patent is extended or adjusted under 35 U.S.C. 154(b) by 75 days.

This patent is subject to a terminal disclaimer.

(21) Appl. No.: 12/004,502

(22) Filed: Dec. 21, 2007

(65) Prior Publication Data
US 2009/0053292 A1    Feb. 26, 2009

Related U.S. Application Data

(60) Continuation of application No. 10/369,299, filed on Feb. 19, 2003, now Pat. No. 7,311,917, which is a division of application No. 09/164,714, filed on Oct. 1, 1998, now Pat. No. 6,541,616.

(51) Int. Cl.
*A61K 39/02* (2006.01)
*C12P 21/04* (2006.01)
*C07H 21/04* (2006.01)
*C07K 14/00* (2006.01)

(52) U.S. Cl. ............... 424/190.1; 424/184.1; 424/234.1; 424/251.1; 536/23.4; 536/23.7; 435/69.7; 530/350

(58) Field of Classification Search ........................ None
See application file for complete search history.

(56) References Cited

U.S. PATENT DOCUMENTS

| | | | |
|---|---|---|---|
| 5,604,131 | A | 2/1997 | Wadsworth et al. |
| 5,607,846 | A | 3/1997 | Murphy et al. |
| 5,808,024 | A | 9/1998 | Sasaki et al. |
| 6,090,576 | A | 7/2000 | Myers et al. |
| 6,214,981 | B1 | 4/2001 | Tucker et al. |
| 7,311,917 | B2 * | 12/2007 | Tucker et al. ............ 424/190.1 |

FOREIGN PATENT DOCUMENTS

| | | |
|---|---|---|
| EP | 0 614 989 | 9/1994 |
| EP | 614989 | 9/1994 |
| WO | WO-93/25708 | 12/1993 |
| WO | WO-95/21922 | 8/1995 |
| WO | WO-96/12733 | 5/1996 |
| WO | WO-96/34960 | 11/1996 |
| WO | WO-97/41731 | 11/1997 |
| WO | WO-99/58563 | 11/1999 |

OTHER PUBLICATIONS

Houghten et al. (Vaccines, 1986, Edited by Fred Brown: Cold Spring Harbor Laboratory).*
Holmes, Exp. Opin.Invest. Drugs, 2001, 10(3):511-519.*
Greenspan et al (Nature Biotechnology, 1999, 7:936-937).*
Ahmed et al., Microbiol. Immunol., 36(6):563-573 (1992).
Ahmed, et al., Microbiol. Immunol. 36(10):1009-1017 (1992).
Ausubel, et al., Eds. 1994, Current Protocols in Molecular Biology, 3: 16.5.1-16.11.10.
Bartos, et al., J. Infect. Dis. 158(4):761-765 (1988).
Bogosian, et al.,"Genome Rearrangements by Residual IS10 Elements in Strains of *Escherichia coli* K-12 Which Had Undergone Tn10 Mutagenesis and Fusaric Acid Selection," Gene. 133(1):17-22.
Burgess, et al., Journal of Cell Biology, 111:2129-2138, 1990.
Catlin, et al., 1990, "*Branhamella catarrhalis*: An Organism Gaining Respect as a Pathogen," Clin Microbil Rev. 3:293-320.
Christensen,et al., Clin Diagn Lab Immunol., Nov. 1996, 3(6): 717-21.
Cohen, 1993, "Naked DNA Points Way to Vaccines," Science, 295(5102): 1691-1692.
Current Protocols in Immunology, 1997, Unit 9.7.5.
Helminen, et al., 1992, "A Major Outer Membrane Protein of *Moraxella catarrhalis* is a Target for Antibodies that Enhance Pulminary Clearance of the Pathogen in an Animal Model," Infect. Immun., 61:2003-2010.
Helminen, et al., 1994, "A Large, Antigenically Conserved Protein on the Surface of *Moraxella catarrhallis* is a Target for Protective Anitbodies," J. Infect. Dis., 170: 867-872.
Inder M. Verma et al., 1CGene Therapy 14promises, problems and prospects 1D, Nature, vol. 389, Sep. 18, 1997, pp. 239 14242.
Jobling, et al., Mol. Microbiol., 1991, 5(7): 1755-67.
Kellens, et al., 1995, "Evidence for Lectin-Mediated Adherence of *Moraxella catarrhalis*," Infection 223:37-41.
Kellens, et al., Infection, 23(1):37/41-41-45 (1995).
Klingman, et al., 1994, "Purification and Characterization of a High Molecular Weight Outer Membrane Protein of *Moraxella (Branhamella) catarrhalis*," Infect Immun 62:1150-1155.

(Continued)

Primary Examiner—Robert B Mondesi
Assistant Examiner—Padma V Baskar
(74) Attorney, Agent, or Firm—K&L Gates LLP

(57) ABSTRACT

The invention discloses the *Moraxella catarrhalis* outer membrane protein polypeptide and polypeptides derived therefrom (collectively "OMP21"), nucleotide sequences encoding said OMP21, and antibodies that specifically bind OMP21. Also disclosed are pharmaceutical compositions including prophylactic or therapeutic compositions, which may be immunogenic compositions including vaccines, comprising OMP21, antibodies thereto or nucleotides encoding same. The invention additionally discloses methods of inducing an immune response to *M. catarrhalis* and OMP21 in an animal, preferably a human, methods of treating and methods of diagnosing *Moraxella* infections in an animal, preferably a human, and kits therefor.

9 Claims, 9 Drawing Sheets

OTHER PUBLICATIONS

Figure 1:
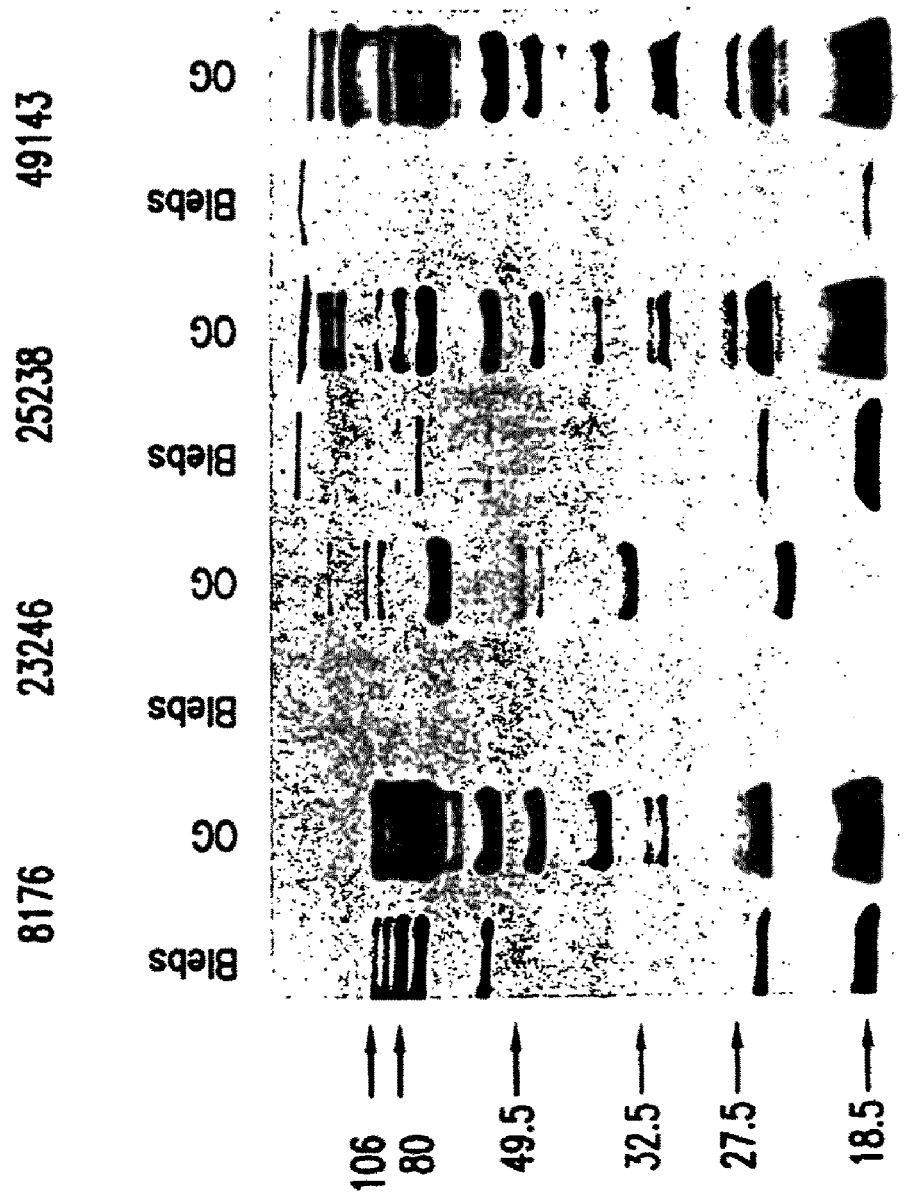

Lazar, et al., Molecular and Cellular Biology, 8(3): 1247-1252, 1988.

Mbaki, et al., 1987, Correlation Between *Branhamella catarrhalis* Adherence to Oropharyngeal Cells and Seasonal Incidence of Lower Respirator Tract Infections, Tohuku J. Exp. Med., 13: 111-121.

McMichael, 2000, Microbes and Infection, 2: 561-568.

Murphy, et al., Infec. Immun. 57(10):293802941 (1989).

Murphy, et al., Microbial Pathogenesis, 6:159-174 (1989).

Murphy, Pediatr. Infect. Dis, 8:S750-S77 (1989).

Murphy, et al., 1993, "The Major Heat-Modifiable Outer Membrane Protein CD is Highly Conserved Among Strains of *Branhamella catarrhalis*," Molec. Microbiol. 10:87-97.

Reece, et al., J. Immunol. 1994, vol. 172, p. 241.

Rikitomi, et al., J. Infect. Dis. 23:559-567 (1991).

Rodinger, et al., "Peptide Hormones," edited by Parsons, J.A., University Park Press, Jun. 1976, 1-5.

Sakuma, et al., NCBI Genbank Accession No. D83266, 1996.

Sarwar, et al., 1992, "Characterization of an Antigenically Conserved Heat-Modifiable Major OUter Membrane Protein of *Branhamella catarrhalis*," Infect Immun, 60:804-809.

Sedegah, et al., 1994, "Protection Against Malaria by Immunication with Plasmid DNA Encoding Circumsporozoite Protein," Proc. Natl. Acad. Sci. USA, 91(21): 9866-9870.

Sedegah, et al., 1998, "Boosting with Recombinant Vaccinia Increases Immunogenicity and Protective Efficacy of Malaria DNA Vaccine," Proc. Natl. Acad. Sci, USA, 95: 7648-7653.

Soto Hernandez, et al., 1989, "Phenotypic Characteristics of *Branhamella catarrhalis* Strains," J. Clin. Microbiol. 27:903-908.

Tucker, et al., 1989, Annual Meeting of Amer. Soc. Microbiol. Abstract. K124.

Ulmer, et al., 1993, "Heterologous Protection Against Influenza by Injection of DNA Encoding a Viral Proten," Science, 259: 1745-1749.

Unhanand, et al., 1992, "Pulmonary Clearance of *Moraxella catarrhalis* in an Animal Model," J. Infect Dis. 165:644-650.

Wang, et al., 1998, "Induction of Antigen-Specific Cytotoxic T Lymphocytes in Humans by a Malaria DNA Vaccine," Science, 282(5388): 476-480.

Japanese Office Action with English translation corresponding to JP Application No. 2000-572357, dated Sep. 1, 2009, 13 pages.

* cited by examiner

```
5'       11         21         31         41         51         61         71         81         91
1   ATGAAAACTT TAAAAACACT ATTGGCAGTA TCAGCTTCTT CGTTATTGGC GATGAGTGCT AACGCTGCCA TCAGCTATGG CAATTCTGCT GATGCCAAC
    TACTTTTGAA ATTTTTGTGA TAACCGTCAT AGTCGAAGAA GCAATAACCG CTACTCACGA TTGCGACGGT AGTCGATACC GTTAAGACGA CTACGGGTTG

5'       11         21         31         41         51         61         71         81         91
101 CCTATGTTGG TGCCAAAATT GGTCAAGTAG ACGCCAAGCA AATCAACGGT AAGAACACCG CTTATGGTAT TTATGCAGGT TATAACTTTG ACCAAAATTT
    GGATACAACC ACGGTTTTAA CCAGTTCATC TGCGGTTCGT TTAGTTGCCA TTCTTGTGGC GAATACCATA AATACGTCCA ATATTGAAAC TGGTTTTAAA

5'       11         21         31         41         51         61         71         81         91
201 TGGCGTAGAA GCCGAATTTG TTGGTTCAGA CGCCAAAGAA TTTAATGCAG GCGTGAGTCC TGTAAAAGGT GATGTGAAGT CTTTTGGTGC TTATGCACA
    ACCGCATCTT CGGCTTAAAC AACCAAGTCT GCGGTTTCTT AAATTACGTC CGCACTCAGG ACATTTTCCA CTACACTTCA GAAAACCACG AATACGTGT

5'       11         21         31         41         51         61         71         81         91
301 TATCGCTATA ACTTCATCAA TACCCCATTT TATGCCAAGG GCAAATTAGG CATTGCTAAG ACTAAAGTAG ATGTTACCAG CCGTAATGCA ACTACATACT
    ATAGCGATAT TGAAGTAGTT ATGGGGTAAA ATACGGTTCC CGTTTAATCC GTAACGATTC TGATTTCATC TACAATGGTC GGCATTACGT TGATGTATGA

5'       11         21         31         41         51         61         71         81         91
401 CAAACAAAAG CGACAAAACC AGCCTAGCAG GCGGTGTTGG TGTTGGCTTT AAACCATTAG CAAATGTGGG CGTTGAAGCA AGCTACAACT ATCTATCAGA
    GTTTGTTTTC GCTGTTTTGG TCGGATCGTC CGCCACAACC ACAACCGAAA TTTGGTAATC GTTTACACCC GCAACTTCGT TCGATGTTGA TAGATAGTCT

5'       11         21         31         41         51         61         71         81         91
501 AGATGCCAAT GCAATTAGTT TGGGCGCTCA TTTGGCTTTT TAA
    TCTACGGTTA CGTTAATCAA ACCCGCGAGT AAACCGAAAA ATT
```

FIG.3

```
N         11         21         31         41         51         61         71         81         91
1  MKTLKTLLAV SASSLLAMSA NAAISYGNSA DAQPYVGAKI GQVDAKQING KNTAYGIYAG YNFDQNFGVE AEFVGSDAKE FNAGVSPVKG DVKSFGAYGT

N         11         21         31         41         51         61         71         81         91
101 YRYNFINTPF YAKGKLGIAK TKVDVTSRNA TTYSNKSDKT SLAGGVGVGF KPLANVGVEA SYNYLSEDAN AISLGAHLAF #
```

FIG.4

MORAXELLA CATARRHALIS PROTEIN, NUCLEIC ACID SEQUENCE AND USES THEREOF

This application is a continuation of U.S. application Ser. No. 10/369,299, filed Feb. 19, 2003, now U.S. Pat. No. 7,311,917, which itself is a divisional of U.S. application Ser. No. 09/164,714, filed Oct. 1, 1998, now U.S. Pat. No. 6,541,616, both of which disclosures are hereby incorporated in their entirety by reference.

1. FIELD OF THE INVENTION

The present invention generally relates to an isolated or substantially purified protein obtainable from the outer membranes of *M. catarrhalis*, called "OMP21" (defined below in Section 3). The invention also encompasses the amino acid sequence thereof, and antibodies, including cytotoxic antibodies, that specifically bind OMP21. The invention further encompasses pharmaceutical compositions, including prophylactic or therapeutic compositions, and which may be immunogenic compositions, including vaccines. The invention additionally provides methods of preventing, treating or ameliorating disorders in mammals related to *M. catarrhalis* infections and for inducing immune responses to *M. catarrhalis*. The invention further provides isolated nucleotide sequences encoding the OMP21, homologous and complementary sequences thereto, vectors having said sequences, host cells containing said vectors, and prophylactic or therapeutic compositions, which may be immunogenic compositions, including vaccines comprising same. Diagnostic methods and kits are also included.

2. BACKGROUND OF THE INVENTION

*Moraxella catarrhalis*, also known as *Moraxella (Branhamella) catarrhalis* or *Branhamella catarrhalis* and formerly known as *Neisseria catarrhalis* or *Micrococcus catarrhalis*, is a gram-negative bacterium frequently found in the respiratory tract of humans. *M. catarrhalis*, originally thought to be a harmless commensal organism, is now recognized as an important pathogen in upper and lower respiratory tract infections in humans. In humans, *M. catarrhalis* causes serious lower respiratory tract infections in adults with chronic lung disease, systemic infections in immunocompromised patients, and otitis media and sinusitis in infants and children (Helminen et al., 1993, Infect. Immun. 61:2003-2010; Catlin, B. W., 1990, Clin. Microbiol. Rev. 3:293-320; and references cited therein). The outer surface components of *Moraxella catarrhalis* have been studied in attempts to understand the pathogenic process of *M. catarrhalis* infections and to develop useful therapeutic treatments and prophylactic measures against such infections. The outer membrane proteins (OMPs) in particular have received considerable attention as possible virulence factors and as potential vaccine antigens. *M. catarrhalis* has over 20 different OMPs with 6 to 8 of these, OMPs A to H, as the predominate species (Murphy and Loeb, 1989, Microbial Pathogen. 6:159-174). The molecular weights of OMPs A to H range from 98 to 21 kD, respectively (Bartos and Murphy, 1988, J. Infect. Dis. 158:761-765; Helminen et al., 1993, Infect. Immun. 61:2003-2010; Murphy et al, 1993, Molecul. Microbiol. 10:87-97; and Sarwar et al, 1992, Infect. Immun. 60:804-809). Comparisons of protein profiles by sodium dodecylsulfate polyacrylamide gel electrophoresis (SDS-PAGE) of outer membrane preparations from 50 *M. catarrhalis* strains show nearly homogeneous patterns of OMPs A to H (Bartos and Murphy, 1988, J. Infect. Dis. 158:761-765).

In intact bacterium or bacterially-derived outer membrane vesicles, several of the above-identified OMPs present surface-exposed epitopes that elicit the production of antibodies that bind the OMPs. These antigenic OMPs include OMP E and OMP G (Murphy and Bartos, 1989, Infect. Immun. 57:2938-2941); OMP C/D (Sarwar et al., 1992, Infect. Immun. 60:804-809); CopB, an 80 kD OMP, (Helminen et al., 1993, Infect. Immun. 61:2003-2010); and UspA (Helminen et al., 1994, J. Infect. Dis. 170:867-872).

The therapeutic potential of antibodies to surface-exposed epitopes of outer-membrane proteins of *M. catarrhalis* is generally examined by the cytotoxic (bactericidal) activity, because there is no animal model of disease. The only natural host for disease caused by *Moraxella* is human. However, others have studied the role of antibodies in an animal model of *Moraxella* lung clearance. The model involved direct bolus inoculation of lungs of BALB/c VAF/Plus mice with a controlled number of *M. catarrhalis* cells and subsequent examination of the rate of pulmonary clearance of the bacteria (Unhanand et al., 1992, J. Infect. Dis. 165:644-650). Different clinical isolates of the *M. catarrhalis* exhibited different rates of clearance, all of which are relatively rapid, that correlated with the level of granulocyte recruitment into the infection site. Passive immunization with a monoclonal antibody directed to a surface-exposed epitope of CopB and UspA increased the rate of pulmonary clearance of *M. catarrhalis* (Helminen et al., 1993, Infect. Immun. 61:2003-2010; Helminen et al., 1994, J. Infect. Dis. 170:867-872). There remains a need for compositions and methods for diagnosis of, as well as, prophylactic and therapeutic treatments for infections caused by *M. catarrhalis*.

The adherence of bacterial pathogens to a host cell surface promotes colonization and initiates pathogenesis. See, E. H. Beachey, 1981, J. Infect. Dis. 143:325-345. Gram-negative bacteria typically express surface lectins that bind to specific oligosaccharides of glycoproteins and/or glycolipids on the host cell surface. Such lectins are often associated with pili or fimbriae. Bacterial adherence can also occur by non-specific binding resulting from hydrophobic and/or charge interaction with the host cell surface.

The mechanism of *M. catarrhalis* adherence to cells of the respiratory tract remains poorly understood. The organism adheres to cultured human nasopharyngeal epithelial cells. Another study suggests that fimbriae may have a role in the adherence to such cells as fimbriae denaturation or treatment with anti-fimbriae antibodies reduced adherence by fimbriated strains. Fimbriae mediated binding, however, cannot be the sole basis of this adherence as the most highly adhering strain, among the several examined, was a non-fimbriated strain. Thus, other unidentified components are involved in the bacteria's adherence.

3. SUMMARY OF THE INVENTION

An object of the present invention is to provide an isolated or substantially purified OMP21 protein of a *M. catarrhalis* strain, wherein the apparent molecular weight is about 16 kD to about 20 kD, as predicted from the deduced amino acid sequence or determined by sodium dodecylsulfate polyacrylamide gel electrophoresis ("SDS-PAGE"). The term "OMP21" as used herein and in the claims is intended to globally encompass: all forms of the protein having molecular weight of 16 kd to 20 kd, including the native, wild-type OMP21 protein obtainable from *M. catarrhalis*, and "OMP21-derived polypeptides", as defined in Section 3.1 herein. Preferably, OMP21 has the sequence of any of SEQ ID Nos.: 1 or 7 or sequences substantially homologous thereto. More preferably, OMP21 is an outer membrane protein. Still more preferably, OMP21 has a nasopharyngeal binding domain.

It is intended that OMP21 obtainable from any commercially available strains and clinical isolates of *Moraxella catarrhalis* is included in this invention, however preferred is OMP21 obtainable from virulent clinical isolates. The OMP21 is at least 70 wt % pure, preferably at least about 90 wt % pure, and may be in the form of an aqueous solution thereof.

Another object of the present invention is to provide an isolated nucleic acid molecule encoding OMP21. Preferred is the nucleic acid sequence wherein the encoded OMP21 comprises the amino acid sequence of any of SEQ ID NOs.: 1 or 7 or sequences substantially homologous thereto. Also included is an isolated nucleic acid molecule comprising a sequence of any of SEQ ID NOs: 2-6 and 8-20, a complementary sequence thereof, sequences substantially homologous thereto, and any fragment thereof; a DNA sequence encoding a deduced amino acid sequence of any of SEQ ID Nos.:1 or 7, the complimentary sequence thereto, sequences substantially homologous thereto, and any fragment thereof; and a nucleic acid sequence which hybridizes to any one of the sequences described above. The nucleic acid that hybridizes under stringent conditions preferably has a sequence identity of about 70% with any of the sequences mentioned above, more preferably about 90%.

Another object, of the invention is to provide a recombinant expression vector adapted for transformation of a host or for delivery of a sequence encoding OMP21 to a host, comprising the nucleic acid molecule of SEQ ID NO: 6, a complementary sequence thereof, sequences substantially homologous thereto, and any fragment thereof. Preferably, the recombinant expression vector is adapted for transformation of a host and comprises an expression means operatively coupled to the nucleic acid molecule for expression by the host of said OMP21. More preferred is the expression vector wherein the expression means includes a nucleic acid portion encoding a leader sequence for secretion or purification from the host of OMP21.

A further aspect of the invention includes a transformed host cell comprising an expression vector described above and OMP21 producible by the transformed host cell.

The invention further encompasses attenuated and/or inactivated cultivars of *M. catarrhalis* wherein the cultivar has been genetically manipulated to have the gene for OMP21 "knocked-out" and therefore non-transcribed (a "deletion-mutant"), so that the adherence by the organism is reduced. Also encompassed in this invention are cultivars of *M. catarrhalis* having a double deletion of OMP21 and OMP106, as described in PCT publication WO 97/41731, which is incorporated herein by reference in its entirety, so that the organism is non-adherent.

The invention further encompasses pharmaceutical compositions, including prophylactic and therapeutic compositions, and which may be immunogenic compositions including vaccines, wherein said immunogenic composition produces an immune response when administered to a host, comprising at least one component selected from the following group:

a) OMP21;
b) a nucleic acid molecule or a fragment or compliment thereof, encoding OMP21;
c) a nucleic acid molecule having the sequence of SEQ ID NO:6, the complimentary sequence thereto, a nucleic acid sequence which hybridizes under stringent conditions thereto, or fragments thereof;
d) OMP21, obtainable from a transformed host comprising an expression vector comprising a nucleic acid molecule as defined in b) or c) and expression means operatively coupled to the nucleic acid molecule for expression by the host of said OMP21;
e) a recombinant vector comprising a nucleic acid or fragment or analog thereof, encoding OMP21; and
f) a transformed cell comprising the vector of e), optionally one or more adjuvants, and optionally a pharmaceutically acceptable carrier or diluent.

The invention further encompasses pharmaceutical compositions, including prophylactic and therapeutic compositions, and which may be immunogenic compositions including vaccines, comprising an attenuated and/or inactivated *M. catarrhalis* cultivar provided herein, optionally an adjuvant, and optionally a pharmaceutically acceptable carrier or diluent.

The invention further encompasses the pharmaceutical compositions described above, optionally in combination with, fused to, or conjugated to another component, which may be an immunogen, and may include but is not limited to: a lipid, a phospholipid, a carbohydrate including a lipopolysaccharide, another protein, and an attenuated or inactivated whole organism, as provided herein or known to those skilled in the art, including but not limited to those described in Section 2 above. Preferred optional components include any *Moraxella, Neisseria, Pseudomonas, Streptococcus*, or *Haemophilus* attenuated or inactivated whole organism, or a protein or a carbohydrate therefrom. Preferred immunogenic compositions, including vaccines, comprise OMP21 in combination with OMP106 and one or more adjuvants.

Also included are methods for producing an immune response in an animal comprising administering to said animal an effective amount of an immunogenic composition described above.

Another aspect of the invention is directed to the antisera raised against any of the immunogenic compositions described above, and the antibodies present in the antisera that specifically bind the immunogens present in the immunogenic composition, including OMP21 or nucleic acid encoding same, and other immunogenic components.

The invention also includes diagnostic reagents which may include any of the above mentioned aspects, such as the isolated OMP21, the nucleic acid molecule encoding OMP21, the immunogenic composition, the antisera, the antibodies, the vector comprising the nucleic acid, and the transformed cell comprising the vector.

Methods and diagnostic kits for detecting OMP21, *M. catarrhalis*, anti-OMP21 antibodies or anti-*M. catarrhalis* antibodies in a test sample are also included, wherein the methods comprise the steps of:

a) contacting a test sample with an antigenic or immunogenic composition of the present invention or antibodies thereto to form antigen:antibody immunocomplexes, and further,
b) detecting any immunocomplexes formed during step a) as an indication of the presence of said antigen or antibodies in a test sample. The methods may further comprise quantitating any said immunocomplexes formed.

The diagnostic kits for detecting OMP21, *M. catarrhalis*, or antibodies thereto, comprise the antibodies and/or the antigenic or immunogenic composition of the present invention, a container means for contacting said antibodies or antigenic or immunogenic composition with a test sample suspected of having said antibodies and reagent means for measuring antigen:antibody immunocomplexes formed between said antigenic or immunogenic composition and said antibodies.

A further aspect of the present invention provides methods for determining the presence of nucleic acids encoding OMP21 in a sample, comprising the steps of:
 a) contacting a sample with the nucleic acid molecule provided herein to produce duplexes comprising the nucleic acid molecule and any nucleic acid molecule encoding the OMP21 in the sample and specifically hybridizable therewith; and
 b) determining the production of duplexes.

The present invention also provides a diagnostic kit and reagents therefor, for determining the presence of nucleic acid encoding OMP21 in a sample, comprising:
 a) the nucleic acid molecule as provided herein;
 b) means for contacting the nucleic acid with the sample to produce duplexes comprising the nucleic acid molecule and any nucleic acid molecule encoding the OMP21 in the sample and specifically hybridizable therewith; and
 b) means for determining the production of duplexes.

Also included in this invention are methods of preventing, treating or ameliorating disorders related to *M. catarrhalis* in an animal, preferably a human, in need of such treatment comprising administering an effective amount of a pharmaceutical composition provided herein. Preferred disorders include a *M. catarrhalis* bacterial infection, otitis media, respiratory infections, sinusitis and pneumonia. Preferred vaccines and pharmaceutical compositions include those formulated for in vivo administration to an animal, preferably a human, to confer protection against disease, or treatment therefor, caused by a strain of *M. catarrhalis*. Also preferred are compositions formulated as a microparticle, capsule, or liposome preparation.

3.1. Definitions and Abbreviations anti-OMP21=anti-OMP21 polypeptide antibody or antiserum
ATCC=American Type Culture Collection
Blebs=naturally occurring outer membrane vesicles of *M. catarrhalis*
immunogen & immnuogenic=capable of provoking a cellular or humoral immune response
kD=kilodaltons
*M. catarrhalis*=M.c.; *Moraxella catarrhalis*; *Moraxella (Branhamella) catarrhalis*; *Branhamella catarrhalis*; *Neisseria catarrhalis*; or *Micrococcus catarrhalis*
OG=n-octyl β-D-glucopyranoside or octyl glucoside
OMP21="wild-type" protein obtainable from outer membranes of *Moraxella catarrhalis*, having a molecular weight of about 16 kD to about 20 kD, as predicted from the deduced amino acid sequence or as determined by SDS-PAGE; and OMP21-derived polypeptides obtainable from any source by any means including chemical synthesis and recombinant synthesis
OMP21-derived polypeptide=any variant or analog of wild-type protein obtainable from outer membranes of *Moraxella catarrhalis*, having a molecular weight or about 16 kD to about 20 kD ("wild-type-OMP21") containing one or more amino acid deletions, insertions or substitutions; any fragment of wild-type-OMP21 or any variant or analog thereof; any chimeric protein comprising a heterologous polypeptide fused to the C-terminal or N-terminal or internal segment of a whole or a portion of wild-type-OMP21 or any fragment, variant or analog thereof
OMP=outer membrane protein
OMPs=outer membrane proteins
PBS=phosphate buffered saline
PA=polyacrylamide gel
polypeptide=a peptide of any length, preferably one having eight or more amino acid residues
SDS=sodium dodecylsulfate
SDS-PAGE=sodium dodecylsulfate polyacrylamide gel electrophoresis Nucleotide or nucleic acid sequences defined herein are represented by one-letter symbols for the bases as follows:

A (adenine)

C (cytosine)

G (guanine)

T (thymine)

U (uracil)

M (A or C)

R (A or G)

W (A or T/U)

S(C or G)

Y (C or T/U)

K (G or T/U)

V (A or C or G; not T/U)

H (A or C or T/U; not G)

D (A or G or T/U; not C)

B (C or G or T/U; not A)

N (A or C or G or T/U) or (unknown)

Peptide and polypeptide sequences defined herein are represented by one-letter or three-letter symbols for amino acid residues as follows:

| 1 letter | 3 letter | amino acid |
| --- | --- | --- |
| A | Ala | (alanine) |
| R | Arg | (arginine) |
| N | Asn | (asparagine) |
| D | Asp | (aspartic acid) |
| C | Cys | (cysteine) |
| Q | Gln | (glutamine) |
| E | Glu | (glutamic acid) |
| G | Gly | (glycine) |
| H | His | (histidine) |
| I | Ile | (isoleucine) |
| L | Leu | (leucine) |
| K | Lys | (lysine) |
| M | Met | (methionine) |
| F | Phe | (phenylalanine) |
| P | Pro | (proline) |
| S | Ser | (serine) |
| T | Thr | (threonine) |
| W | Trp | (tryptophan) |
| Y | Tyr | (tyrosine) |
| V | Val | (valine) |
| X | Xaa | (unknown) |

The present invention may be more fully understood by reference to the following detailed description of the invention, non-limiting examples of specific embodiments of the invention and the appended figures.

4. BRIEF DESCRIPTION OF THE FIGURES

FIG. 1: Denaturing PAGE comparison of outer membrane protein profiles of *M. catarrhalis* blebs or octyl glucoside (OG) extracts of whole *M. catarrhalis* cells. The numbers over the lanes (81176, 23246, 25238 and 49143) refer to the ATCC strain designations. A prestained SDS-PAGE standard (BioRad catalog #161-0305) was used as molecular weight markers. The standard consisted of the following polypeptides with their approximate molecular weights noted in parenthesis: rabbit muscle phosphorylase B (106 kD); bovine serum albumin (80 kD); hen egg white ovalbumin (49.5 kD) bovine carbonic anhydrase (32.5 kD), soybean trypsin inhibitor (27.5 kD); hen egg white lysozyme (18.5 kD). The positions of the molecular weight markers in the gel are noted on the left side of the drawing by arrows with the molecular weights (kD) of some of the markers above the arrows.

Figure 2:
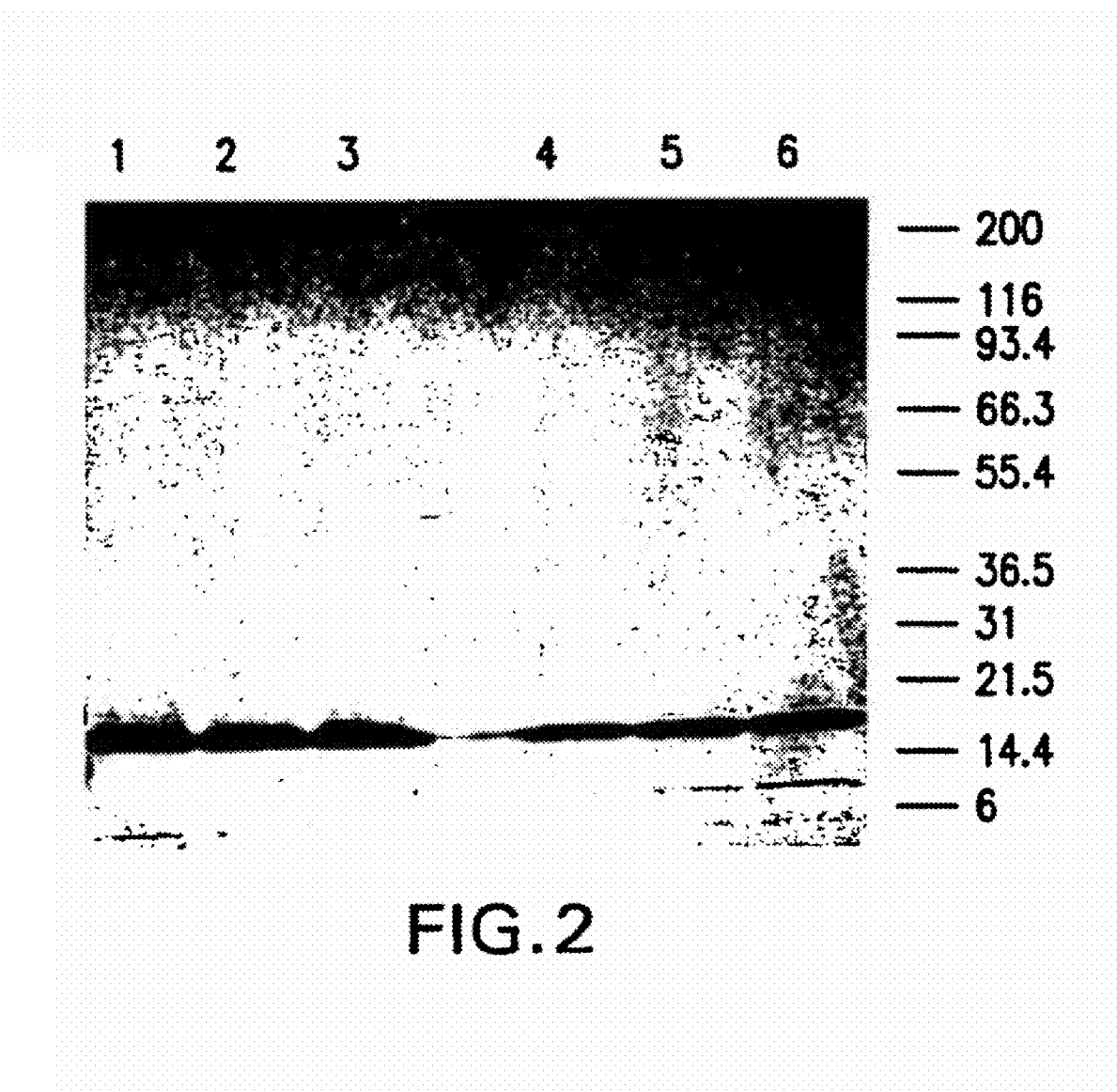

FIG. 2: Molecular weight estimation of OMP21 in a 4-20% gradient denaturing polyacrylamide gel in the presence of a reducing agent using OMP21 purified from ATCC strain 49143 that were incubated in sample buffer at either 25° C. (Lanes 1-3) or 100° C. (Lanes 4-6) prior to application to the gel. Proteins in the gel were visualized by reductive silver staining. A broad range SDS-PAGE standard (NOVEX, catalog #LC5677) was used as molecular weight markers (shown on left). The standards consisted of the following polypeptides (approximate molecular weights noted in parenthesis): rabbit skeletal muscle myosin (200 kD); *E. coli* β-galactosidase (116 kD); phosphorylase B (97.4 kD); bovine serum albumin (66.2 kD); glutamic dehydrogenase (55.4 kD); lactate dehydrogenase (36.5 kD); carbonic anhydrase (31 kD); trypsin inhibitor (21.5 kD); lysozyme (14.4 kD); and aprotinin (6 kD). The positions of the molecular weight markers in the gel are noted on the left side of the figure by lines with the molecular weights (kD) of the markers above the lines.

FIG. 3: Determined nucleic acid sequence of OMP21 from *M. catarrhalis* strain 49143 (SEQ ID NO: 6).

FIG. 4: Deduced amino acid sequence of OMP21 from *M. catarrhalis* strain 49143 (SEQ ID NO: 7).

Figure 5:
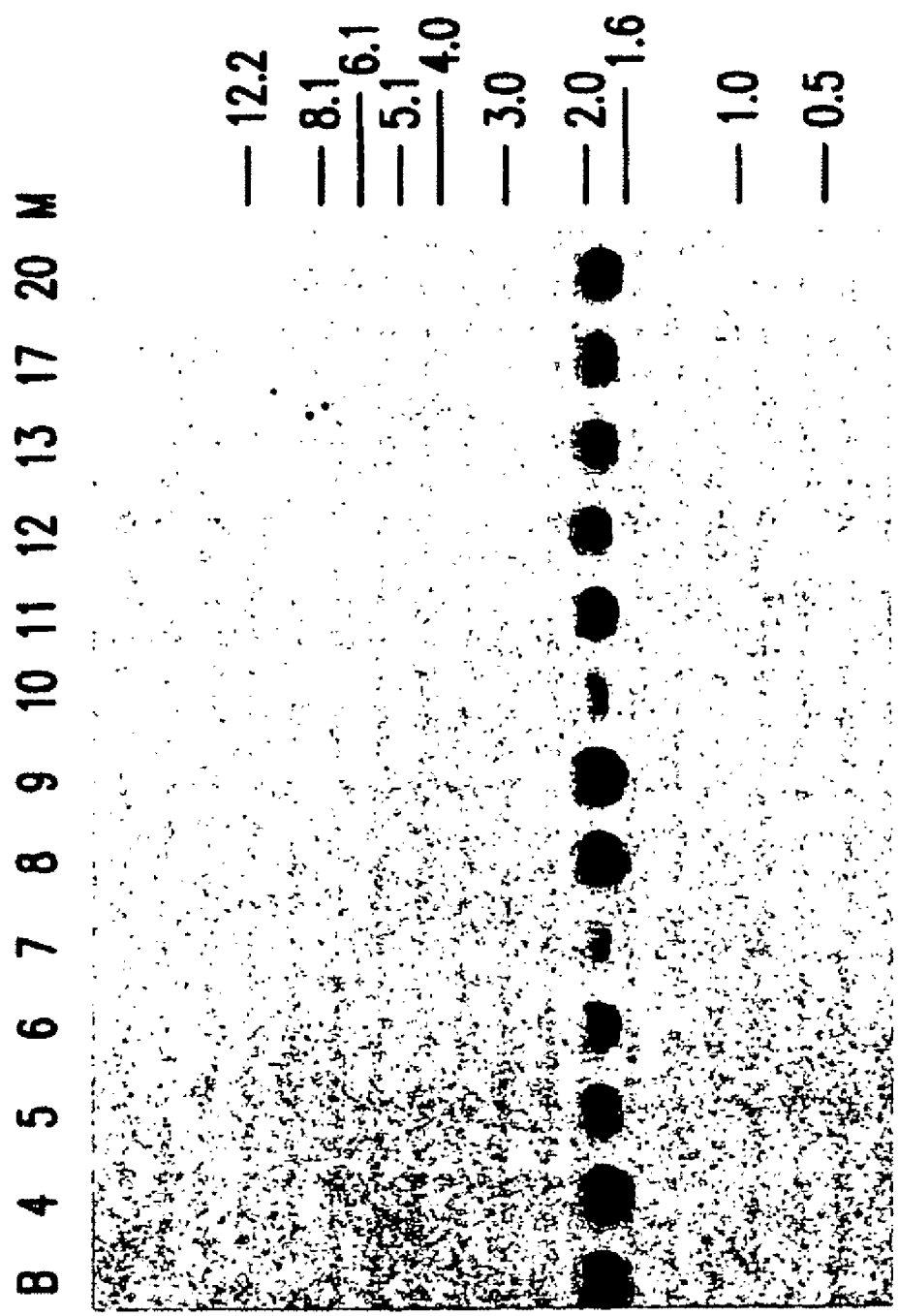

FIG. 5: RFLP Southern blot analysis of HindIII restriction endonuclease digests of *M. catarrhalis* chromosomal DNA as described in the Example in Section 11. The first lane contains size markers (M); the other lanes (B, 4, 5, 6, 7, 8, 9, 10, 11, 12, 13, 17, 20) contain the hybridizing bands to the digests that all have an approximate size of 1.8 kb.

Figure 6:
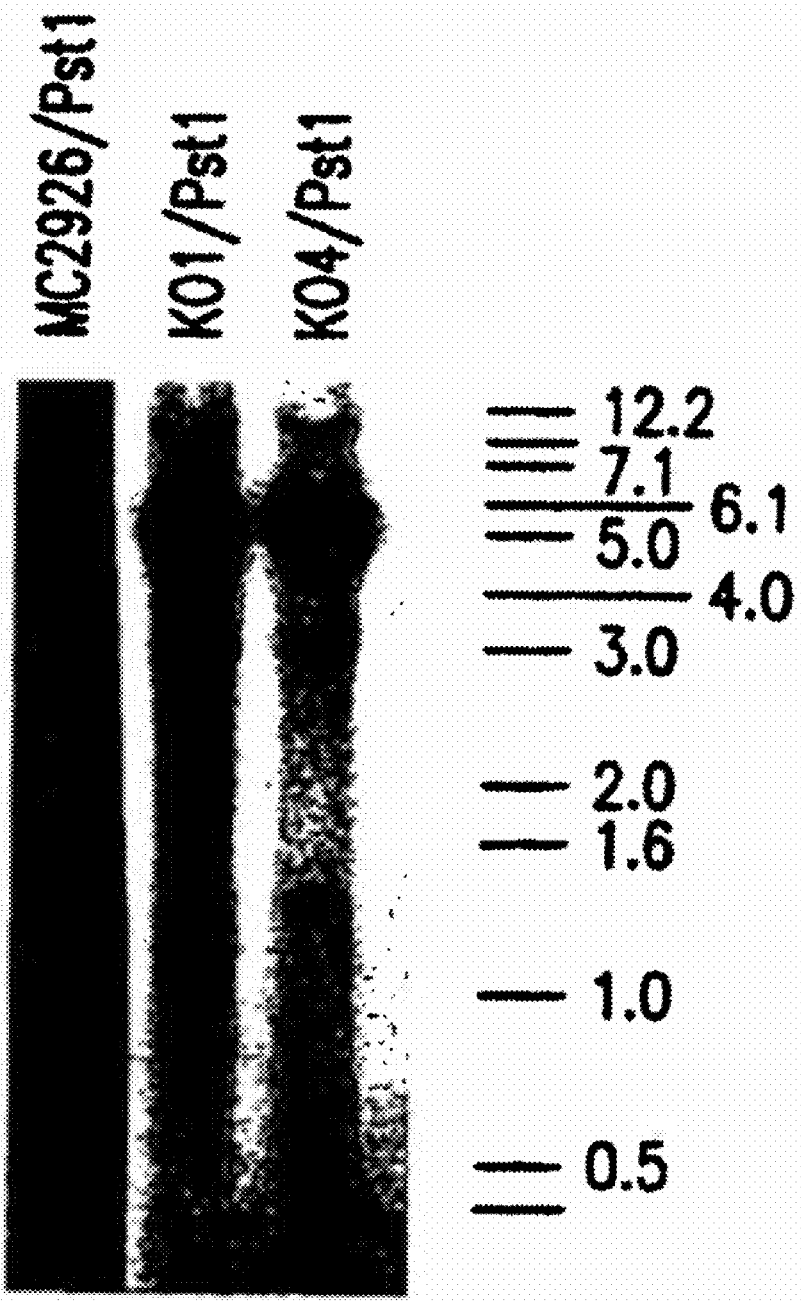

FIG. 6: Southern blot analysis of PstI restriction endonuclease digests of *M. catarrhalis* wild-type and OMP21 deletion-mutant (knock-out) DNA as described in the Example in Section 10.5. Using the probe described, a 8 kb DNA fragment is detected in PstI digests of wild-type *M. catarrhalis* DNA (MC2926). The same probe detects a 4.5 kb DNA fragment in digests of the knock-outs (KO1, KO4). Size markers are indicated on the left.

Figure 7A:
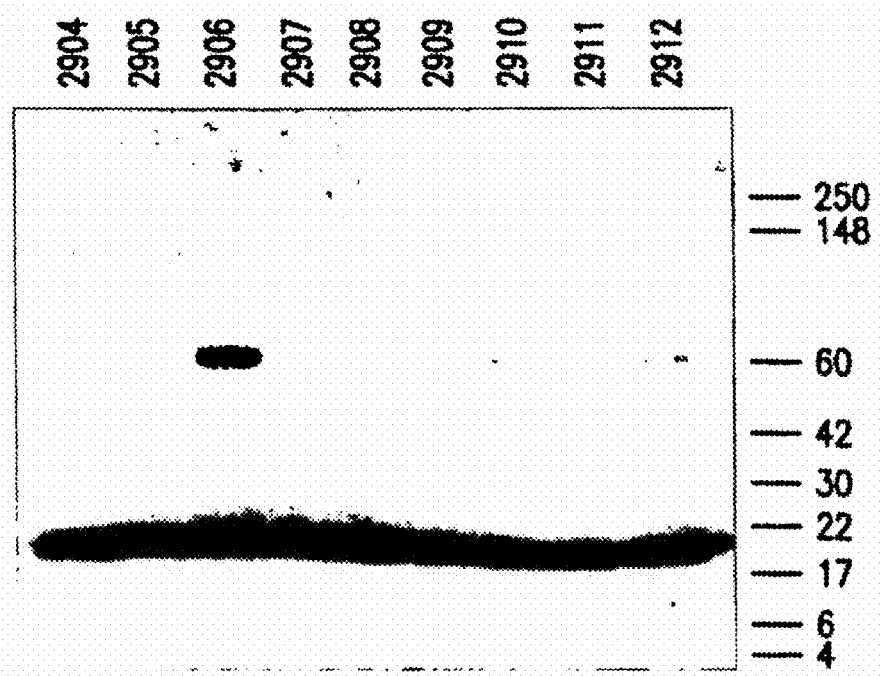
Figure 7B:
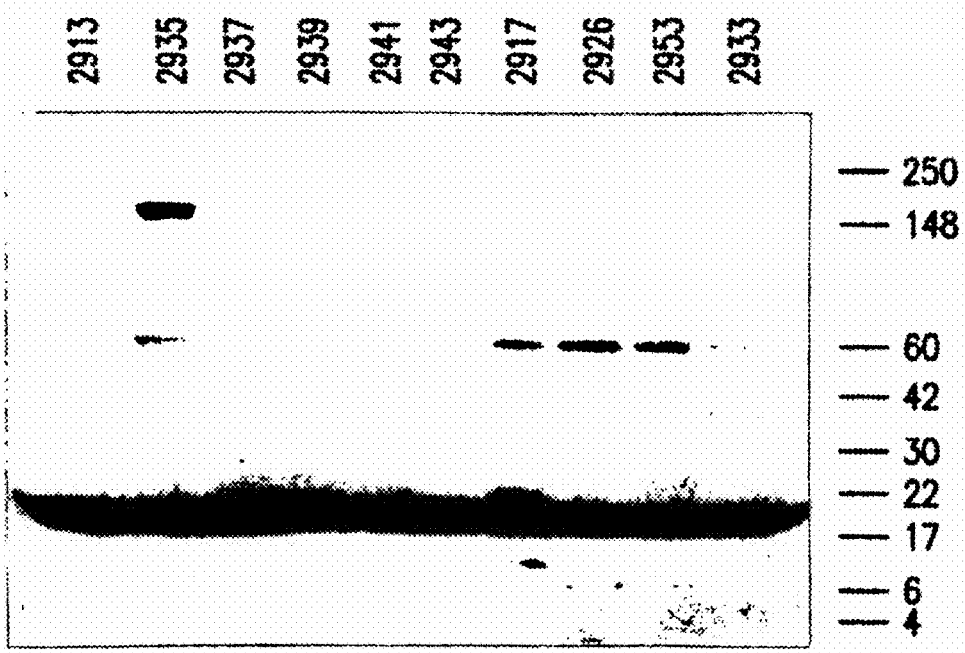

FIGS. 7A and 7B: Western Blots of protein extracts of several *M. catarrhalis* strains (shown in both 7A (top panel) and 7B (bottom panel)) using a rabbit antiserum to OMP21 (the location of the OMP21 polypeptide is indicated by the arrow) as the probe. The prestained molecular weight markers (NOVEX, catalog #LC5725) consisted of the following polypeptides (approximate molecular weights noted in parenthesis): myosin (250 kD); phosphorylase B (148 kD); glutamic dehydrogenase (60 kD); carbonic anhydrase (42 kD); myoglobin (30 kD); lysozyme (17 kD); aprotinin (6 kD); and insulin (4 kD).

Figure 8:
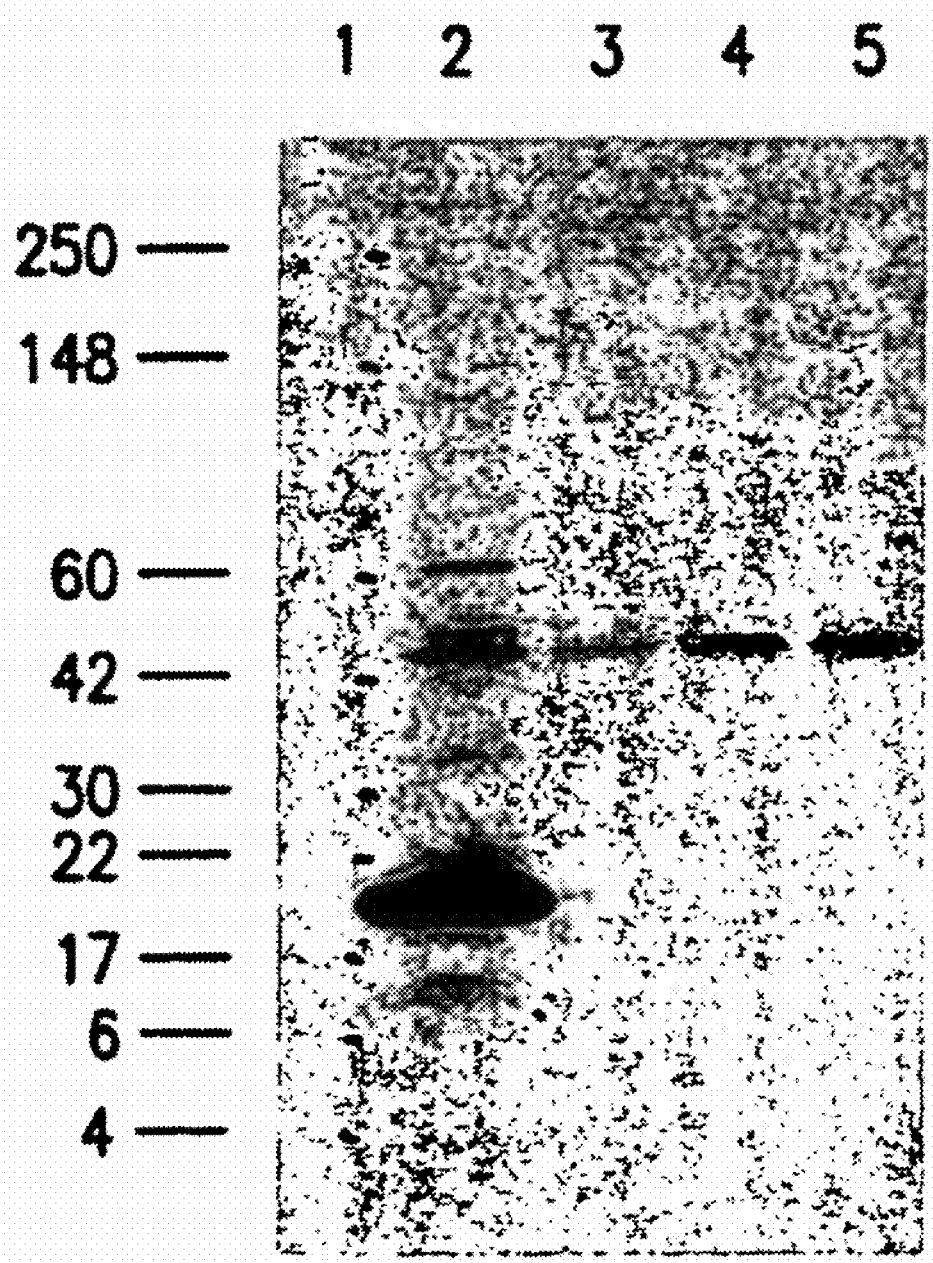

FIG. 8: Western Blot of protein extracts of OMP21-deletion mutants of *M. catarrhalis* using a rabbit antiserum to OMP21 as the probe. Octyl glucoside extracts of the parent strain (Lane 2) and OMP21 deletion mutant *M. catarrhalis* strains (Lanes 3-5). The transfer and Western blot procedures and molecular weight markers (Lane 1) used were identical to those used to obtain the blots shown in FIGS. 7A and B.

Figure 9:
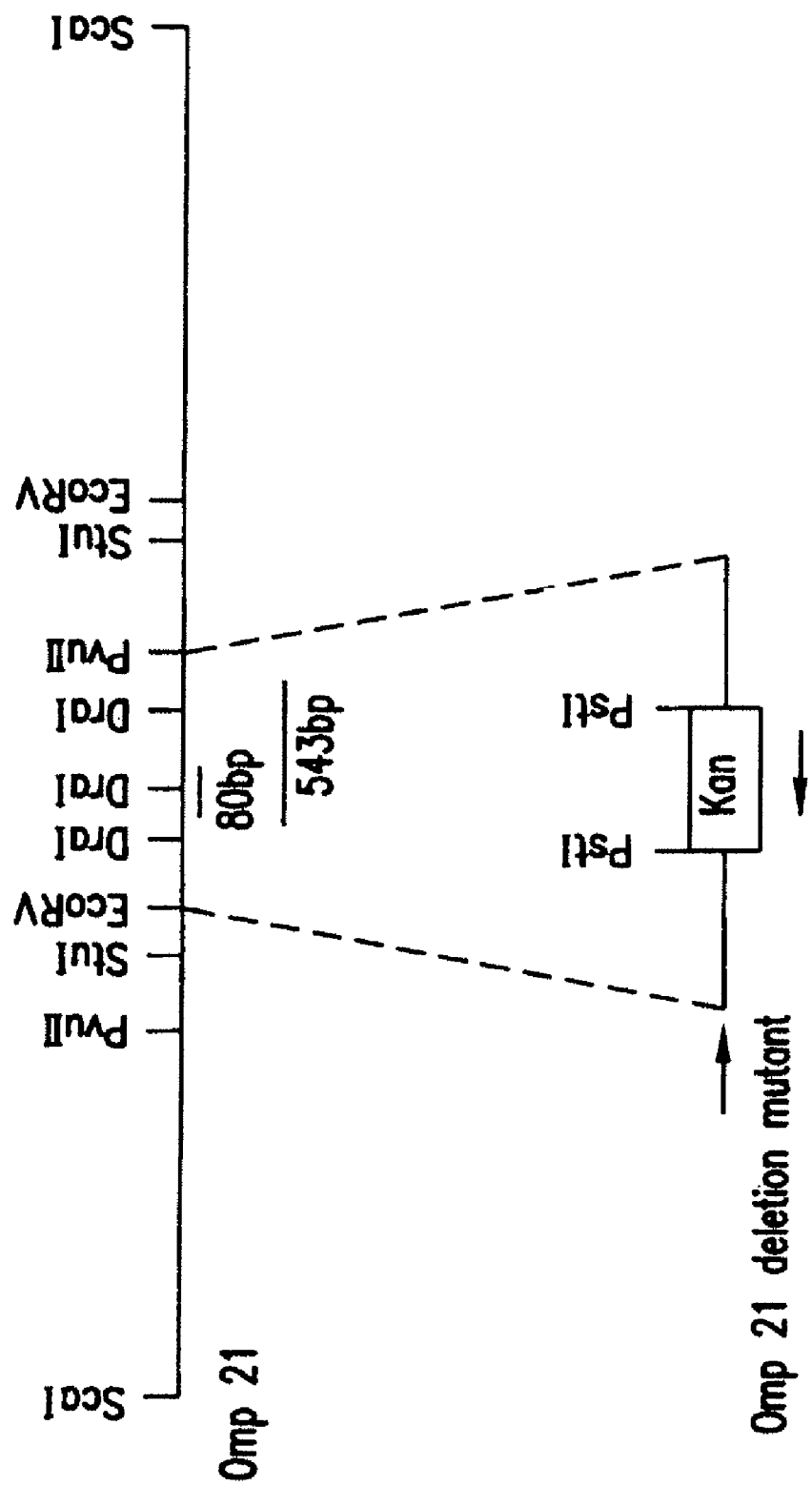

FIG. 9: Map of OMP21 and OMP21 deletion mutants. The organization of the omp 21 locus in the wild-type strain compared to the structure imposed on the locus after the gene-targeting construct has been inserted by homologous recombination is shown. The map also shows restriction endonuclease cleavage sites as well as DNA fragments of 80 bp and 543 bp described in the Examples below.

5. DETAILED DESCRIPTION OF THE INVENTION

5.1. OMP21 Polypeptide

OMP21 polypeptide of the invention is the outer membrane protein of a *M. catarrhalis* strain or cultivar that has an apparent molecular weight in SDS-PAGE of about 16 kD to about 20 kD. According to the invention, an outer membrane protein of *M. catarrhalis* is a polypeptide that is present in *M. catarrhalis* blebs, or that can be extracted from *M. catarrhalis* blebs or intact cells by a detergent, such as but not limited to any n-octyl β-D-glucopyranoside (OG), EmpigenBB™ (N-dodecyl-N,N-dimethyl-glycine, CalBiochem) and sarkosyl, in buffer solution at room temperature. See Murphy and Loeb, 1989, Microbial Pathogenesis 6:159-174, for a discussion of *M. catarrhalis* blebs, which are naturally occurring vesicles consisting of the outer membrane of *M. catarrhalis*.

OMP21 polypeptide may also be identified as the polypeptide in extract of *M. catarrhalis* blebs or intact cells that has an apparent molecular weight of about 16 kD to about 20 kD as determined by denaturing gel electrophoresis in PA with SDS, using formulations as described in Harlow and Lane (Antibodies: A Laboratory Manual, Cold Spring Harbor Laboratory Press, Cold Spring Harbor, N.Y., Appendix I, 1988). In a particular embodiment, OMP21 polypeptide in the detergent extract of *M. catarrhalis* strain ATCC 49143 has an apparent molecular weight of about 16-20 kD. Heat treatment of the detergent extract at 100° C. for 5 minutes does not modify the apparent molecular weight of OMP21 polypeptide as determined by SDS-PAGE in 4-20% gradient PAG with a reducing agent (β-mercaptoethanol) using formulations described in Harlow and Lane, supra. See FIG. 2.

In particular embodiments, the OMP21 polypeptide is that obtainable from any of *M. catarrhalis* strains including, but not limited to, ATCC 49143, ATCC 25238, ATCC 25240, ATCC 43617, ATCC 43618, ATCC 43627 and ATCC 43628. The preferred source of OMP21 polypeptide is ATCC 49143.

In a particular embodiment, OMP21 comprises, preferably at the amino-terminal, the amino acid sequence AISYGN-SADAQPYVGAKIGQVDAKQINGKNTAYGIYAGYN (SEQ ID NO:1) or a sequence substantially homologous thereto. In another particular embodiment, OMP21 comprises the deduced amino acid sequence (SEQ ID NO:7) or a sequence substantially homologous thereto.

As used herein, a "substantially homologous" sequence is at least 80%, preferably greater than 80%, more preferably greater than 90% identical to a reference sequence of identical size or when compared to a reference sequence when the alignment or comparison is conducted by a computer homology program or search algorithm known in the art. By way of example and not limitation, useful computer homology programs include the following: Basic Local Alignment Search Tool (BLAST) (www.ncbi.nlm.nih.gov) (Altschul et al., 1990, J. of Molec. Biol., 215:403-410, "The BLAST Algorithm; Altschul et al., 1997, Nuc. Acids Res. 25:3389-3402) a heuristic search algorithm tailored to searching for sequence similarity which ascribes significance using the statistical methods of Karlin and Altschul 1990, Proc. Nat'l Acad. Sci.

USA, 87:2264-68; 1993, Proc. Nat'l Acad. Sci. USA 90:5873-77. Five specific BLAST programs perform the following tasks:

1) The BLASTP program compares an amino acid query sequence against a protein sequence database.

2) The BLASTN program compares a nucleotide query sequence against a nucleotide sequence database.

3) The BLASTX program compares the six-frame conceptual translation products of a nucleotide query sequence (both strands) against a protein sequence database.

4) The TBLASTN program compares a protein query sequence against a nucleotide sequence database translated in all six reading frames (both strands).

5) The TBLASTX program compares the six-frame translations of a nucleotide query sequence against the six-frame translations of a nucleotide sequence database.

Smith-Waterman (database: European Bioinformatics Institute wwwz.ebi.ac.uk/bic_sw/) (Smith-Waterman, 1981, J. of Molec. Biol., 147:195-197) is a mathematically rigorous algorithm for sequence alignments.

FASTA (see Pearson et al., 1988, Proc. Nat'l Acad. Sci. USA, 85:2444-2448) is a heuristic approximation to the Smith-Waterman algorithm. For a general discussion of the procedure and benefits of the BLAST, Smith-Waterman and FASTA algorithms see Nicholas et al., 1998, "A Tutorial on Searching Sequence Databases and Sequence Scoring Methods" (www.psc.edu) and references cited therein.

According to various aspects of the invention, the polypeptides of the invention are characterized by their apparent molecular weights based on the polypeptides' migration in SDS-PAGE relative to the migration of known molecular weight markers. While any molecular weight standards known in the art may be used with the SDS-PAGE, preferred molecular weight markers comprise carbonic anhydrase, trypsin inhibitor and lysozyme. One skilled in the art will appreciate that the polypeptides of the invention may migrate differently in different types of gel systems (e.g., different buffers; different types and concentrations of gel, crosslinker or SDS). One skilled in the art will also appreciate that the polypeptides may have different apparent molecular weights due to different molecular weight markers used with the SDS-PAGE. Hence, the molecular weight characterization of the polypeptides of the invention is intended to be directed to cover the same polypeptides on any SDS-PAGE systems and with any molecular weight markers which might indicate slightly different apparent molecular weights for the polypeptides than those disclosed here.

5.2. OMP21-Derived Polypeptides

OMP21-derived polypeptides are intended to be encompassed by the term OMP21, and may be a fragment of the OMP21 polypeptide having 6 or more amino acids, preferably 8 or more amino acids, more preferably 9 or more amino acids, still more preferably 10 or more amino acids. The intact OMP21 polypeptide may contain one or more amino acid residues that are not necessary to its immunogenicity. It may be the case, for example, that only the amino acid residues forming a particular epitope of the OMP21 polypeptide are necessary for immunogenic activity. Unnecessary amino acid sequences can be removed by techniques well known in the art. For example, the unwanted amino acid sequences can be removed by limited proteolytic digestion using enzymes such as trypsin, papain, or related proteolytic enzymes or by chemical cleavage using agents such as cyanogen bromide and followed by fractionation of the digestion or cleavage products.

An OMP21-derived polypeptide of the invention may also be a modified OMP21 polypeptide or fragment thereof (i.e., an OMP21 polypeptide or fragment having one or more amino acid substitutions, insertions and/or deletions of the wild-type OMP21 sequence). Such modifications may enhance the immunogenicity of the resultant polypeptide product or have no effect on such activity. Modification techniques that may be used include those disclosed in U.S. Pat. No. 4,526,716.

As an illustrative, non-limiting example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

An OMP21-derived polypeptide of the invention may also be a molecule comprising a region that is substantially homologous to (e.g., in various embodiments, at least 60% or 70% or 80% or 90% or 95% identity over an amino acid sequence of identical size or when compared to an aligned sequence in which the alignment is performed by a computer homology program known in the art) or whose encoding nucleic acid is capable of hybridizing to a coding OMP21 sequence, under highly stringent, moderately stringent, or low or nonstringent conditions.

By way of example and not limitation, useful computer homology programs include the following: Basic Local Alignment Search Tool (BLAST) (www.ncbi.nlm.nih.gov) (Altschul et al., 1990, J. of Molec. Biol., 215:403-410, "The BLAST Algorithm; Altschul et al., 1997, Nuc. Acids Res. 25:3389-3402) a heuristic search algorithm tailored to searching for sequence similarity which ascribes significance using the statistical methods of Karlin and Altschul (1990, Proc. Nat'l Acad. Sci. USA, 87:2264-68; 1993, Proc. Nat'l Acad. Sci. USA 90:5873-77). Two specific BLAST programs perform the following tasks:

1) The BLASTP program compares an amino acid query sequence against a protein sequence database; and 2) The BLASTN program compares a nucleotide query sequence against a nucleotide sequence database; and hence are useful to identify, respectively, substantially homologous amino acid and nucleotide sequences.

Additional algorithms which can be useful are the Smith-Waterman and FASTA algorithms. See supra, Section 5.1.

Included within the scope of the invention are OMP21-derived polypeptides which are OMP21 polypeptide fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Furthermore, if desired, nonclassical amino acids or chemical amino acid analogs can be introduced as a substitution or addition into the OMP21 polypeptide sequence. Nonclassical amino acids include but are not limited to the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

An OMP21-derived polypeptide may further be a chimeric polypeptide comprising one or more heterologous polypeptides fused to the amino-terminal or carboxyl-terminal or internal of a complete OMP21 polypeptide or a portion of or a fragment thereof. Useful heterologous polypeptides comprising such chimeric polypeptide include, but are not limited to, a) pre- and/or pro-sequences that facilitate the transport, translocation and/or processing of the OMP21-derived polypeptide in a host cell, b) affinity purification sequences, and c) any useful immunogenic sequences (e.g., sequences encoding one or more epitopes of a surface exposed protein of a microbial pathogen).

Preferably, the OMP21-derived polypeptides of the invention are immunologically cross-reactive with wild-type-OMP21, thus being capable of eliciting in an animal an immune response to M. catarrhalis. More preferably, the OMP21-derived polypeptides of the invention comprise sequences forming one or more outer surface epitopes of the native OMP21 polypeptide of M. catarrhalis (i.e., the surface exposed epitopes of OMP21 polypeptide as it exists in intact M. catarrhalis cells). Such preferred OMP21-derived polypeptides can be identified by their ability to specifically bind antibodies raised to intact M. catarrhalis cells (e.g., antibodies elicited by formaldehyde or glutaraldehyde fixed M. catarrhalis cells; such antibodies are referred to herein as "anti-whole cell" antibodies). For example, polypeptides or peptides from a limited or complete protease digestion of the OMP21 polypeptide are fractionated using standard methods and tested for their ability to bind anti-whole cell antibodies. Reactive polypeptides comprise preferred OMP21-derived polypeptides. They are isolated and their amino acid sequences determined by methods known in the art.

These preferred OMP21-derived polypeptides also can be identified by using anti-whole cell antibodies to screen bacterial libraries expressing random fragments of M. catarrhalis genomic DNA or cloned nucleotide sequences encoding the OMP21 polypeptide. See, e.g., Sambrook et al., Molecular Cloning, A Laboratory Manual, 2nd ed., Cold Spring Harbor Press, NY, Vol. 1, Chapter 12. The reactive clones are identified and their inserts are isolated and sequenced to determine the amino acid sequences of such preferred OMP21-derived polypeptides.

5.3. Isolation and Purification of OMP21

The invention provides isolated OMP21. As used herein, the term "isolated" means that the product is significantly free of other biological materials with which it is naturally associated. That is, for example, an isolated OMP21 is between about 70% and 94% pure OMP21 by weight. Preferably, OMP21 of the invention is purified. As used herein, the term "purified" means that OMP21 is substantially free of other biological material with which it is naturally associated. That is, a purified OMP21 is at least 95% pure OMP21 by weight, preferably at least 98% pure OMP21 by weight, and most preferably at least 99% pure OMP21 by weight.

The OMP21 of the invention may be isolated from protein extracts including whole cell extract, of any M. catarrhalis strain or cultivar. Preferably, the protein extract is a detergent extract of outer membrane vesicles (i.e., blebs) or whole cells of M. catarrhalis including, but not limited to, any of strains ATCC 49143, ATCC 25238, ATCC 25240, ATCC 43617, ATCC 43618, ATCC 43627 and ATCC 43628. The preferred source of such extracts is ATCC 49143. Another source of the OMP21 is protein preparations from gene expression systems expressing cloned sequences encoding OMP21 (see Section 5.8., infra).

OMP21 can be isolated and purified from the source material using any biochemical technique and approach well known to those skilled in the art. In one approach, M. catarrhalis outer membrane is obtained by standard techniques and outer membrane proteins are solubilized using a solubilizing compound such as a detergent. A preferred solubilizing solution is one containing about 1.5% octyl glucopyranoside w/v (OG). Another preferred solubilizing solution is one containing about 1.0% EmpigenBB™ (N-dodecyl-N,N-dimethyl-glycine, CalBiochem). OMP21 is in the solubilized fraction. Cellular debris and insoluble material in the extract are separated and removed preferably by centrifuging. The polypeptides in the extract are concentrated, incubated in SDS-containing Laemmli gel sample buffer at 100° C. for 5 minutes and then fractionated by electrophoresis in a 4-20% gradient denaturing SDS-PAGE. See Laemmli, 1970, Nature 227:680-685. The band or fraction identified as OMP21 as described above (e.g., the silver-stained polypeptide band that is present in the detergent extract) may then be isolated directly from the fraction or gel slice containing the OMP21. In a preferred embodiment, OMP21 has an apparent molecular weight of 16 to about 20 kD as determined by comparing its migration distance or rate in a denaturing SDS-PAGE relative to those of trypsin inhibitor (21.5 kD) and lysozyme (14.4 kD).

Another method of purifying OMP21 is by affinity chromatography using anti-OMP21 antibodies, (see Section 5.5). Preferably, monoclonal anti-OMP21 antibodies are used. The antibodies are covalently linked to agarose gels activated by cyanogen bromide or succinamide esters (Affi-Gel, BioRad, Inc.) or by other methods known to those skilled in the art. The protein extract is loaded on the top of the gel as described above. The contact is for a period of time and under standard reaction conditions sufficient for OMP21 to bind to the antibody. Preferably, the solid support is a material used in a chromatographic column. OMP21 is then removed from the antibody, thereby permitting the recovery OMP21 in isolated, or preferably, purified form.

OMP21 fragments can be produced by chemical and/or enzymatic cleavage or degradation of isolated or purified OMP21. OMP21 can also be chemically synthesized based on the known amino acid sequence of OMP21 and, in the case of a chimeric polypeptide, those of the heterologous polypeptide by methods well known in the art. See, for example, Creighton, 1983, Proteins: Structures and Molecular Principles, W.H. Freeman and Co., NY.

OMP21 can also be produced in a gene expression system expressing a recombinant nucleotide construct comprising sequences encoding OMP21. The nucleotide sequences encoding polypeptides of the invention may be synthesized, and/or cloned, and expressed according to techniques well known to those skilled in the art. See, for example, Sambrook, et al., 1989, Molecular Cloning, A Laboratory Manual, Vols. 1-3, Cold Spring Harbor Press, NY, Chapter 9.

OMP21 can be fractionated and purified by the application of standard protein purification techniques, modified and applied in accordance with the discoveries and teachings described herein. In particular, preferred OMP21 fragments, those that form an outer surface epitope of the native OMP21, may be isolated and purified according to the affinity procedures disclosed above for the isolation and purification of OMP21 (e.g., affinity purification using anti-OMP21 antibodies).

If desirable, the polypeptides of the invention may be further purified using standard protein or peptide purification techniques including but are not limited to electrophoresis, centrifugation, gel filtration, precipitation, dialysis, chromatography (including ion exchange chromatography, affinity chromatography, immunoadsorbent affinity chromatography, reverse-phase high performance liquid chromatography, and gel permeation high performance liquid chromatography), isoelectric focusing, and variations and combinations thereof.

One or more of these techniques may be employed sequentially in a procedure designed to separate molecules according to their physical or chemical characteristics. These characteristics include the hydrophobicity, charge, binding capability, and molecular weight of the protein. The various fractions of materials obtained after each technique are tested for their molecular weight or their abilities to bind anti-OMP21 antibodies. Those fractions showing such activity are then subjected to the next technique in the sequential procedure, and the new fractions are tested again. The process is repeated until only one fraction having the above described characteristics remains and that fraction produces only a single band or entity when subjected to polyacrylamide gel electrophoresis or chromatography.

5.4. OMP21 Immunogens and Anti-OMP21 Antibodies

As used herein and in the claims, "antibodies" of the invention may be obtained by any conventional methods known to those skilled in the art, such as but not limited to the methods described in Antibodies A Laboratory Manual (E. Harlow, D. Lane, Cold Spring Harbor Laboratory Press, 1989) which is incorporated herein by reference in its entirety. The term "antibodies" is intended to include all forms, such as but not limited to polyclonal, monoclonal, purified IgG, IgA, IgM and fragments thereof.

The present invention provides antibodies that specifically bind OMP21. For the production of such antibodies, an immunogenically effective amount of a composition comprising at least one isolated or preferably, purified component selected from the following group:

a) OMP21;

b) a nucleic acid molecule or a fragment or compliment thereof, encoding OMP21;

c) a nucleic acid molecule having the sequence of SEQ ID NO: 6, the complimentary sequence thereto, a nucleic acid sequence which hybridizes under high stringency conditions thereto, or fragments thereof;

d) OMP21, obtainable from a transformed host comprising an expression vector comprising a nucleic acid molecule as defined in b) or c) and expression means operatively coupled to the nucleic acid molecule for expression by the host of said OMP21;

e) a recombinant vector comprising a nucleic acid or fragment or analog thereof, encoding OMP21;

f) a transformed cell comprising the vector of e), optionally one or more adjuvants, and optionally a pharmaceutically acceptable carrier or diluent therefor are administered to an animal.

The above mentioned compositions may further include optionally in combination with, fused to, or conjugated to another component, which may be an immunogen, including a lipid, a phospholipid, a carbohydrate, including a lipopolysaccharide, another protein, and an attenuated or inactivated whole organisms, as provided herein or known to those skilled in the art, including but not limited to those described in Section 2 above. Preferred optional components include any *Moraxella, Neisseria* or *Haemophilus* protein. Preferred immunogenic compositions, including vaccines, comprise isolated OMP21 in combination with OMP106 and one or more adjuvants.

In an embodiment, the OMP21 is separated from other outer membrane proteins present in the detergent extract of outer membrane of *M. catarrhalis* cells or blebs using SDS-PAGE (see Section 5.2. above) and the gel slice containing OMP21 is used as the immunogen and injected into a rabbit to produce antisera containing polyclonal OMP21-antibodies. The same immunogen can be used to immunize mice and guinea pigs for the production of polyclonal antibodies or mice for the production of hybridoma lines that produce monoclonal anti-OMP21 antibodies. In particular embodiments, a PA slice containing isolated or purified OMP21 from any of strains ATCC 49143, ATCC 25238, ATCC 25240, ATCC 43617, ATCC 43618, ATCC 43627 and ATCC 43628 is used as the immunogen. In preferred embodiments, a PA slice containing isolated or purified OMP21 from strain ATCC 49143 is used as the immunogen.

In other embodiments, a peptide fragment of OMP21 is used as an immunogen. Preferably, a peptide fragment of purified OMP21 or a chemically synthesized peptide fragment of OMP21 is used. The peptides may be produced by protease digestion, chemical cleavage of isolated or purified OMP21 or chemical synthesis and then may be isolated or purified. Such isolated or purified peptides can be used directly as immunogens. In particular embodiments, useful peptide fragments include but are not limited to those having the sequence AISYGNSADAQPYVGAKIGQVDAK-QINGKNTAYGIYAGYN (SEQ ID NO: 1) or any portion thereof that is 6 or more amino acids in length. In an another embodiment, the peptide has the sequence as shown in FIG. 4 (SEQ ID NO: 7).

Useful immunogens may also comprise OMP21 conjugated to a carrier molecule, preferably a carrier protein. Carrier proteins may be any commonly used in immunology, include, but are not limited to, bovine serum albumin (BSA), chicken albumin, keyhole limpet hemocyanin (KLH) and the like. For a discussion of hapten protein conjugates, see, for example, Hartlow, et al., Antibodies: A Laboratory Manual, Cold Spring Harbor Laboratory Press, Cold Spring Harbor, N.Y., 1988, or a standard immunology textbook such as Roitt, I. et al., IMMUNOLOGY, C. V. Mosby Co., St. Louis, Mo. (1985) or Klein, J., IMMUNOLOGY, Blackwell Scientific Publications, Inc., Cambridge, Mass., (1990).

In yet another embodiment, for the production of antibodies that specifically bind one or more outer surface epitopes of OMP21, intact *M. catarrhalis* cells or blebs prepared therefrom are used as immunogen. The cells or blebs may be fixed with agents such as formaldehyde or glutaraldehyde before immunization. See Harlow and Lane, Antibodies: A Laboratory Manual, Cold Spring harbor Laboratory Press, Cold Spring Harbor, N.Y., 1988, Chapter 15. It is preferred that such anti-whole cell antibodies be monoclonal antibodies.

Hybridoma lines producing the desired monoclonal antibodies can be identified by using purified OMP21 as the screening ligand. Cells or blebs of any *M. catarrhalis* strain including, but not limited to, ATCC 49143, ATCC 25238, ATCC 25240, ATCC 43617, ATCC 43618, ATCC 43627 and ATCC 43628 are used as the immunogen for inducing these antibodies. Preferably, cells or blebs of strain ATCC 49143 are used as the immunogen for inducing these antibodies.

In general, an animal (a wide range of vertebrate species can be used, the most common being humans, mice, rats, guinea pig, hamsters and rabbits) is immunized with the OMP21, nucleic acid sequence thereof or immunogenic fragment or derivative thereof of the present invention in the absence or presence of an adjuvant or any agent that would enhance the immunogen's effectiveness and boosted at regular intervals. The animal serum is assayed for the presence of desired antibody by any convenient method. The serum or blood of said animal can be used as the source of polyclonal antibodies.

Polyclonal antibodies produced by whole cell or bleb immunizations contain antibodies that bind other *M. catarrhalis* outer membrane proteins ("non-anti-OMP21 antibodies") and thus are more cumbersome to use where it is known or suspected that the sample contains other *M. catarrhalis* outer membrane proteins or materials that are cross-reactive with these other outer membrane proteins. Under such circumstances, any binding by the anti-whole cell antibodies of a given sample or band must be verified by coincidental binding of the same sample or band by antibodies that specifically bind OMP21 (e.g., anti-OMP21), or by competition tests using anti-OMP21 antibodies or OMP21 as the competitor (i.e., addition of anti-OMP21 antibodies or OMP21 to the reaction mix lowers or abolishes sample binding by anti-whole cell antibodies). Alternatively, such polyclonal antisera, containing "non-anti-OMP21" antibodies, may be cleared of such antibodies by standard approaches and methods. For example, the non-anti-OMP21 antibodies may be removed by precipitation with cells of deletion-mutant *M. catarrhalis* cultivars or *M. catarrhalis* strains known not to have the OMP21; or by absorption to columns comprising such cells or outer membrane proteins of such cells.

In further embodiments, useful immunogens for eliciting antibodies of the invention comprise mixtures of two or more of any of the above-mentioned individual immunogens, preferred are mixtures of OMP21 and OMP106.

Immunization of animals with the immunogens described herein, preferably humans, rabbits, guinea pigs, chinchillas, rats, mice, sheep, goats, cows or horses, is performed following procedures well known to those skilled in the art, for purposes of obtaining antisera containing polyclonal antibodies or hybridoma lines secreting monoclonal antibodies.

Monoclonal antibodies can be prepared by standard techniques, given the teachings contained herein. Such techniques are disclosed, for example, in U.S. Pat. No. 4,271,145 and U.S. Pat. No. 4,196,265. Briefly, an animal is immunized with the immunogen.

As a general method for isolating monoclonal antibodies, when an acceptable antibody titre is detected, the animal is euthanized and the spleen is aseptically removed for fusion. The spleen cells are mixed with a specifically selected immortal myeloma cell line, and the mixture is then exposed to an agent, typically polyethylene glycol or the like, which promotes the fusion of cells. Under these circumstances fusion takes place in a random selection and a fused cell mixture together with unfused cells of each type is the resulting product. The myeloma cell lines that are used for fusion are specifically chosen such that, by the use of selection media, such as HAT: hypoxanthine, aminopterin, and thymidine, the only cells to persist in culture from the fusion mixture are those that are hybrids between cells derived from the immunized donor and the myeloma cells. After fusion, the cells are diluted and cultured in the selective media. The culture media is screened for the presence of antibody having desired specificity towards the chosen antigen. Those cultures containing the antibody of choice are cloned by limiting dilution until it can be adduced that the cell culture is single cell in origin. Other methods for generating monoclonal antibodies are now known and such methods are included in this invention; for instance, recombinant monoclonal antibodies selected from recombinant bacteria are also included.

Immunization regimens for production of both polyclonal and monoclonal antibodies are well known in the art. The immunogen may be administered by any of a number of routes, including subcutaneous, intravenous, intraperitoneal, intradermal, intramuscular, mucosal, or a combination of these. The immunogen may be administered in soluble form, aggregate form, and optionally attached to or mixed with a physical carrier and/or an adjuvant, using methods and materials well known in the art. The antisera and antibodies may be purified using column chromatography methods well known to those of skill in the art.

According to the present invention, OMP21s of *M. catarrhalis* strains are immuno-cross reactive. Thus, antibodies raised to OMP21 of one *M. catarrhalis* strain or cultivar specifically bind OMP21 of other *M. catarrhalis* strains and cultivars. For example, polyclonal anti-OMP21 antibodies induced by OMP21 of strain ATCC 49143 specifically bind not only the homologous OMP21 (i.e., the OMP21 of strain ATCC 49143) but also OMP21 of other *M. catarrhalis* strains including, but not limited to, ATCC 43628, ATCC 43627, ATCC 43618, ATCC 43617, ATCC 25240 and ATCC 25238.

The antibodies of the invention, including but not limited to anti-OMP21 antibodies, can be used to facilitate isolation and purification of OMP21. The antibodies may also be used as probes for identifying clones in expression libraries that have inserts encoding OMP21. The antibodies may also be used in immunoassays (e.g., ELISA, RIA, Westerns) to specifically detect and/or quantitate *M. catarrhalis* in biological specimens.

The antibodies of the invention, particularly those which are cytotoxic, may also be used in passive immunization to prevent or attenuate *M. catarrhalis* infections of animals, including humans. (As used herein, a cytotoxic antibody is one which enhances opsonization and/or complement killing of the bacterium bound by the antibody). An effective concentration of polyclonal or monoclonal antibodies raised against one or more of the immunogens of the invention may be administered to a host to achieve such effects. The exact concentration of the antibodies administered will vary according to each specific antibody preparation, but may be determined using standard techniques well known to those of ordinary skill in the art. Administration of the antibodies may be accomplished using a variety of techniques, including, but not limited to those described in Section 5.5. for the delivery of vaccines.

5.5. Pharmaceutical Compositions

The present invention also provides pharmaceutical compositions, including therapeutic and prophylactic compositions, which may be immunogenic compositions including vaccines, useful for treating, preventing or ameliorating *M. catarrhalis* infections of animals, including humans. Preferred pharmaceutical compositions are vaccines.

The pharmaceutical compositions are preferably vaccines, and can be prepared by techniques known to those skilled in the art and comprise, for example, an immunologically or therapeutically effective amount of any of the OMP21 immunogens disclosed in Section 5.4., optionally in combination with or fused to or conjugated to one or more other immunogens including lipids, phospholipids, carbohydrates including lipopolysaccharides, and other proteins of *Moraxella* or other bacterial origin, entire organisms or subunits thereof, a pharmaceutically acceptable carrier, possibly an appropriate adjuvant, and possibly other materials traditionally found in pharmaceutical compositions, including vaccines.

Preferred other immunogens include any *Moraxella, Neisseria, Pseudomonas, Streptococcus*, or *Haemophilus* attenuated or inactivated whole organism, or a protein or a carbohydrate therefrom. More preferred immunogenic compositions, including vaccines, are cocktail vaccines that comprise OMP21 in combination with OMP106 and one or more adjuvants, or Hin47 as described in U.S. Pat. No. 5,679,547 (incorporated herein by reference in its entirety). Such a cocktail vaccine has the advantage that immunity against several pathogens can be obtained by a single administration. Examples of other immunogens are those used in the known DPT vaccines.

According to another embodiment, the vaccines of the invention comprise an immunologically effective amount of any of the immunogens disclosed in Section 5.4., and additionally an inactivated or attenuated *M. catarrhalis* cultivar of the invention. An inactivated or attenuated *M. catarrhalis* cultivar is obtained using any methods known in the art including, but not limited to, chemical treatment (e.g., formalin), heat treatment and irradiation. A vaccine which contains antigenic material of only one pathogen is a monovalent vaccine. Vaccines which contain antigenic material of several pathogens are combined vaccines and are also encompassed by the present invention. Such combined vaccines contain, for example, material from various pathogens or from various strains of the same pathogen, or from combinations of various pathogens.

The vaccine may also contain one or more adjuvants to improve or enhance or efficiently induce humoral immune responses (HIR) and cell-mediated immunity (CMI). Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Desirable characteristics of ideal adjuvants include:

(1) lack of toxicity;

(2) ability to stimulate a long-lasting immune response;

(3) simplicity of manufacture and stability in long-term storage;

(4) ability to elicit both CMI and HIR to antigens administered by various routes, if required;

(5) synergy with other adjuvants;

(6) capability of selectively interacting with populations of antigen presenting cells (APC);

(7) ability to specifically elicit appropriate $T_H1$ or $T_H2$ cell-specific immune responses; and (8) ability to selectively increase appropriate antibody isotype levels (for example, IgA) against antigens.

Immunostimulatory agents or adjuvants have been used for many years. Intrinsic adjuvants, such as lipo-polysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and a HBsAg vaccine has been adjuvanted with alum. While the usefulness of alum is well established for some applications, it has limitations. For example, alum is ineffective for influenza vaccination and inconsistently elicits a cell mediated immune response.

Other extrinsic adjuvants may include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes.

U.S. Pat. No. 4,855,283 granted to Lockhoff et al on Aug. 8, 1989 which is incorporated herein by reference, teaches glycolipid analogues including N-glycosylamides, N-glycosylureas and N-glycosylcarbamates, each of which is substituted in the sugar residue by an amino acid, as immunomodulators or adjuvants. Thus, Lockhoff et al. (U.S. Pat. No. 4,855,283), reported that N-glycosphospholipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, (incorporated herein by reference), teaches that octadecyl tyrosine hydrochloride (OTH) functioned as an adjuvant when complexed with tetanus toxoid and formalin inactivated type I, II and III poliomyelitis virus vaccine. Lipidation of synthetic peptides has also been used to increase their immunogenicity.

Therefore, according to the invention, the pharmaceutical compositions comprising OMP21 may further comprise an adjuvant, such as, but not limited to alum, QS21, heat labile toxin from enterotoxigenic *E. coli* (LT), Cholera toxin (CT), or Bacille Calmette-Guerine (BCG) and mutated or modified forms of the above.

The term "immunologically effective amount" is used herein to mean an amount sufficient to induce a cellular or humoral immune response. The amount needed will vary depending upon the immunogenicity of the OMP21 and the species and weight of the subject to be vaccinated, but may be ascertained using standard techniques known in the art in view of the teachings provided herein. Preferably, the vaccine elicits an immune response in a subject which produces antibodies including anti-OMP21 antibodies and more preferably, antibodies that neutralize bacterial binding, are opsonizing or are bactericidal. More preferably the immune response is one that can prevent *M. catarrhalis* infections or attenuate the severity of any preexisting or subsequent *M. catarrhalis* infections. In preferred, non-limiting, embodiments of the invention, an effective amount of vaccine produces an elevation of anti-bacterial antibody titer to at least two, more preferably three, times the antibody titer prior to vaccination.

In general, the quantity of immunogen will be between 0.1 and 500 micrograms per dose. In a preferred, specific, non-limiting embodiment of the invention, approximately 0.1 to 100 µg and preferably 10 to 50 µg are administered to a host. The compositions of the present invention may also further comprise a suitable pharmaceutical carrier. The carriers are known to those skilled in the art and include stabilizers, diluents, excipients and buffers. Suitable stabilizers include carbohydrates, such as sorbitol, lactose, mannitol, starch, sucrose, dextran, and glucose and proteins, such as albumin or casein. Suitable diluents include saline, Hanks Balanced Salts, and Ringers solution. Such excipients may include, water, saline, dextrose, glycerol, ethanol, and combinations thereof. Suitable buffers include an alkali metal phosphate, an alkali metal carbonate, or an alkaline earth metal carbonate. Other suitable pharmaceutical carriers are described in Remington's Pharmaceutical Sciences, Mack Publishing Company, a standard reference text in this field, which is incorporated herein by reference in its entirety.

The vaccines of the invention are prepared by techniques known to those skilled in the art, given the teachings contained herein. Generally, an immunogen is mixed with a carrier to form a solution, suspension, or emulsion. One or more of the additives discussed above may be in the carrier or may be added subsequently. The vaccine preparations may be desiccated, for example, by freeze drying for storage purposes. If so, they may be subsequently reconstituted into liquid vaccines by the addition of an appropriate liquid carrier.

The vaccines are administered to humans or other animals. They can be administered in one or more doses. Suitable regimes for initial administration and booster doses are also variable, but may include an initial administration followed by subsequent administrations. The dose may also depend on the route of administration and will vary according to the size of the host. These compositions can take the form of solutions, suspensions, tablets, pills, capsules, sustained release formulations or powders, etc., and may contain about 0.0001 to 95 wt % of the OMP21, preferably 0.001 to 10 wt %. The vaccines may be administered by known routes of administration. Many methods may be used to introduce the vaccine formulations described here. These methods include but are not limited to intradermal, intramuscular, intraperitoneal, intravenous, subcutaneous, oral (intragastric), intranasal, intravaginal or intrarectal routes and other mucosal routes. Alternatively, other modes of administration including suppositories and oral formulations may be desirable. The preferred routes are intramuscular or subcutaneous injection.

5.6. Methods of Detecting

The OMP21 is useful as an antigen in immunoassays including enzyme-linked immunosorbent assays (ELISA), RIAs and other non-enzyme linked antibody binding assays or procedures known in the art for the detection of antibacterial, anti-*M. catarrhalis*, and anti-OMP21 protein antibodies in a test sample. In ELISA assays, the OMP21 is immobilized onto a selected surface, for example, a surface capable of binding proteins such as the wells of a polystyrene microtiter plate. After washing to remove incompletely absorbed OMP21, a nonspecific protein such as a solution of bovine serum albumin (BSA) that is known to be antigenically neutral with regard to the test sample may be bound to the selected surface. This allows for blocking of nonspecific absorption sites on the immobilizing surface and thus reduces the background caused by nonspecific binding of antisera onto the surface.

The immobilizing surface is then contacted with a test sample to be tested in a manner conducive to immune complex (antigen/antibody) formation. Test samples may include human fluids or solid samples, including but not limited to human blood, serum, plasma, saliva, urine, stool, sputum, and any other clinically isolated fluid samples, such as from an infected ear, and/or biological materials, etc. This may include diluting or solubilizing the sample with a diluent, such as a solution of BSA, bovine gamma globulin (BGG) and/or phosphate buffered saline (PBS)/Tween. The sample is then allowed to incubate for from 2 to 4 hours, at temperatures such as of the order of about 20° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound OMP21, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG.

To provide detecting means, the second antibody may have an associated activity such as an enzymatic activity that will generate, for example, a color development upon incubating with an appropriate chromogenic substrate. Quantification may then be achieved by measuring the degree of color generation using, for example, a visible spectrophotometer.

Another embodiment includes diagnostic kits comprising all of the essential reagents required to perform a desired immunoassay according to the present invention. The diagnostic kit may be presented in a commercially packaged form as a combination of one or more containers holding the necessary reagents. Such a kit may comprise a *Moraxella* bacterium or antigenic portion thereof, a monoclonal or polyclonal antibody of the present invention in combination with several conventional kit components. Conventional kit components will be readily apparent to those skilled in the art and are disclosed in numerous publications, including Antibodies A Laboratory Manual (E. Harlow, D. Lane, Cold Spring Harbor Laboratory Press, 1989) which is incorporated herein by reference in its entirety. Conventional kit components may include such items as, for example, microtitre plates, buffers to maintain the pH of the assay mixture (such as, but not limited to Tris, HEPES, etc.), conjugated second antibodies, such as peroxidase conjugated anti-mouse IgG (or any anti-IgG to the animal from which the first antibody was derived) and the like, and other standard reagents.

5.7. Nucleic Acids Encoding OMP21

The present invention also provides nucleic acids encoding OMP21. The nucleotide sequence comprising the entire OMP21 open reading frame is depicted in FIG. 3, and SEQ ID NO:6. A deduced amino acid sequence encoded by the open reading frame of OMP21 is depicted in FIG. 4, and SEQ ID NO:7.

Nucleic acids of the present invention can be single or double stranded. The invention also provides nucleic acids hybridizable to or complementary to the foregoing sequences. In specific aspects, nucleic acids are provided which comprise a sequence complementary to at least 10, 25, 50, 100, 200, or 250 contiguous nucleotides of a nucleic acid encoding an OMP21 polypeptide or an OMP21-derived polypeptide. In a specific embodiment, a nucleic acid which is hybridizable to a nucleic acid encoding OMP21 polypeptide (e.g., having sequence SEQ. ID. NO.: 10 or 12), or to a nucleic acid encoding an OMP21-derived polypeptide, under conditions of low stringency is provided.

By way of example and not limitation, procedures using such conditions of low stringency are as follows (see also Shilo and Weinberg, 1981, Proc. Natl. Acad. Sci. USA 78:6789-6792): Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10$^6$ cpm $^{32}$P-labeled probe is used. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and re-exposed to film. Other conditions of low stringency which may be used are well known in the art (e.g., as employed for cross-species hybridizations).

In another specific embodiment, a nucleic acid which is hybridizable to a nucleic acid encoding OMP21 polypeptide or an OMP21-derived polypeptide under conditions of high stringency is provided. By way of example and not limitation, procedures using such conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5-20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art.

In another specific embodiment, a nucleic acid which is hybridizable to a nucleic acid encoding OMP21 polypeptide or an OMP21-derived polypeptide under conditions of moderate stringency is provided.

Various other stringency conditions which promote nucleic acid hybridization can be used. For example, hybridization in 6×SSC at about 45° C., followed by washing in 2×SSC at 50° C. may be used. Alternatively, the salt concentration in the wash step can range from low stringency of about 5×SSC at 50° C., to moderate stringency of about 2×SSC at 50° C., to high stringency of about 0.2×SSC at 50° C. In addition, the temperature of the wash step can be increased from low stringency conditions at room temperature, to moderately stringent conditions at about 42° C., to high stringency conditions at about 65° C. Other conditions include, but are not limited to, hybridizing at 68° C. in 0.5M NaHPO$_4$ (pH7.2)/1 mM EDTA/7% SDS, or hybridization in 50% formamide/ 0.25 M NaHPO$_4$ (pH 7.2)/0.25 M NaCl/1 mM EDTA/7% SDS; followed by washing in 40 mM NaHPO$_4$ (pH 7.2)/1 mM EDTA/5% SDS at 42° C. or in 40 mM NaHPO$_4$ (pH7.2) 1 mM EDTA/1% SDS at 50° C. Both temperature and salt may be varied, or alternatively, one or the other variable may remain constant while the other is changed.

Low, moderate and high stringency conditions are well known to those of skill in the art, and will vary predictably depending on the base composition of the particular nucleic acid sequence and on the specific organism from which the nucleic acid sequence is derived. For guidance regarding such conditions see, for example, Sambrook et al., 1989, Molecular Cloning, A Laboratory Manual, Second Edition, Cold Spring Harbor Press, N.Y., pp. 9.47-9.57; and Ausubel et al., 1989, Current Protocols in Molecular Biology, Green Publishing Associates and Wiley Interscience, N.Y.

Nucleic acids encoding NMAP-derived polypeptides, including but not limited to fragments or a portion thereof, (see Section 5.2), and OMP21 antisense nucleic acids are additionally provided. As is readily apparent, as used herein, a "nucleic acid encoding a fragment or portion of a nucleic acid encoding OMP21 polypeptide or an OMP21-derived polypeptide" shall be construed as referring to a nucleic acid encoding only the recited fragment or portion of the nucleic acid encoding OMP21 polypeptide or an OMP21-derived polypeptide and not the other contiguous portions of the nucleic acid encoding OMP21 polypeptide or an OMP21-derived polypeptide protein as a continuous sequence.

Also encompassed are nucleotide sequences substantially homologous to the above described nucleic acids. As used herein a "substantially homologous" sequence is at least 70%, preferably greater than 80%, more preferably greater than 90% identical to a reference sequence of identical size or when the alignment or comparison is conducted by a computer homology program or search algorithm known in the art.

By way of example and not limitation, useful computer homology programs include the following: Basic Local Alignment Search Tool (BLAST) (www.ncbi.nlm.nih.gov) (Altschul et al., 1990, J. Molec. Biol., 215:403-410, "The BLAST Algorithm; Altschul et al., 1997, Nuc. Acids Res. 25:3389-3402) a heuristic search algorithm tailored to searching for sequence similarity which ascribes significance using the statistical methods of Karlin and Altschul (1990, Proc. Nat'l Acad. Sci. USA, 87:2264-68; 1993, Proc. Nat'l Acad. Sci. USA 90:5873-77). Five specific BLAST programs are provided and the BLASTN program compares a nucleotide query sequence against a nucleotide sequence database. Additional algorithms which can be useful are the Smith-Waterman and FASTA algorithms. See Section 5.1.

In one aspect, the nucleic acids of the invention may be synthesized using methods known in the art. Specifically, a portion of or the entire amino acid sequence of OMP21 may be determined using techniques well known to those of skill in the art, such as via the Edman degradation technique (see, e.g., Creighton, 1983, Proteins: Structures and Molecular Principles, W.H. Freeman & Co., N.Y., pp. 34-49). The amino acid sequence obtained is used as a guide for the synthesis of DNA encoding OMP21 from oligonucleotides using conventional chemical approaches or polymerase chain reaction (PCR) amplification of overlapping DNA fragments.

In another aspect, the amino acid sequence may be used as a guide for the synthesis of degenerate oligonucleotides which in turn can be used to screen for OMP21 coding sequences in M. catarrhalis genomic libraries. Such libraries may be prepared by isolating DNA from cells of any M. catarrhalis strain. Preferably the DNA used as the source of the OMP21 polypeptide coding sequence, for both genomic libraries and PCR amplification, is prepared from cells of any M. catarrhalis strain including, but not limited to, ATCC 49143, ATCC 25238, ATCC 25240, ATCC 43617, ATCC 43618, ATCC 43627 and ATCC 43628.

In the preparation of genomic libraries, DNA fragments are generated, some of which will encode parts or the whole of M. catarrhalis OMP21. The DNA may be cleaved at specific sites using various restriction enzymes. Alternatively, one may use DNase in the presence of manganese to fragment the DNA, or the DNA can be physically sheared, as for example, by sonication. The DNA fragments can then be separated according to size by standard techniques, including but not limited to, agarose and polyacrylamide gel electrophoresis, column chromatography and sucrose gradient centrifugation. The DNA fragments can then be inserted into suitable vectors, including but not limited to plasmids, cosmids, bacteriophages lambda or $T_4$, and yeast artificial chromosome (YAC). (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) The genomic library may be screened by nucleic acid hybridization to labeled probe (Benton and Davis, 1977, Science 196:180; Grunstein and Hogness, 1975, Proc. Natl. Acad. Sci. U.S.A. 72:3961).

The genomic libraries may be screened with a labeled degenerate oligonucleotide as a screening probe corresponding to the amino acid sequence or any complement thereof of any peptide of OMP21 using optimal approaches well known in the art. or fragments may be used as the probe. Any probe used preferably is 15 nucleotides or longer.

Clones in libraries with insert DNA encoding OMP21 will hybridize to one or more of the degenerate oligonucleotide probes. Hybridization of such oligonucleotide probes to genomic libraries are carried out using methods known in the art. For example, hybridization may be carried out in 2×SSC, 1.0% SDS at 50° C. and washed using the same conditions.

In yet another aspect, clones of nucleotide sequences encoding a part or the entire OMP21 may also be obtained by screening *M. catarrhalis* expression libraries. For example, *M. catarrhalis* DNA is isolated and random fragments are prepared and ligated into an expression vector (e.g., a bacteriophage, plasmid, phagemid or cosmid) such that the inserted sequence in the vector is capable of being expressed by the host cell into which the vector is then introduced. Various screening assays can then be used to select for the expressed OMP21. In one embodiment, the various anti-OMP21 antibodies of the invention (see Section 5.5) can be used to identify the desired clones using methods known in the art. See, for example, Harlow and Lane, 1988, Antibodies: A Laboratory Manual, Cold Spring Harbor Laboratory Press, Cold Spring Harbor, N.Y., Appendix IV. Clones or plaques from the library are brought into contact with the antibodies to identify those clones that bind.

In an embodiment, colonies or plaques containing DNA that encodes OMP21 could be detected using DYNA Beads according to Olsvick et al., 29th ICAAC, Houston, Tex. 1989, incorporated herein by reference. Anti-OMP21 antibodies are crosslinked to tosylated DYNA Beads M280, and these antibody-containing beads would then be used to adsorb to colonies or plaques expressing OMP21 on the particle or colony surface. Colonies or plaques expressing OMP21 are identified as any of those that bind the beads.

Alternatively, the anti-OMP21 antibodies can be nonspecifically immobilized to a suitable support, such as silica or Celite resin. This material would then be used to adsorb to bacterial colonies expressing OMP21 as described in the preceding paragraph.

In another aspect, PCR amplification may be used to produce substantially pure DNA encoding a part of or the whole of OMP21 from *M. catarrhalis* genomic DNA. Oligonucleotide primers, degenerate or otherwise, corresponding to known OMP21 polypeptide amino-terminal sequences can be used as 5' primers. Oligonucleotide sequences, degenerate or otherwise, that are reverse complements of DNA sequences encoding the carboxy-terminal are used as the 3' primer.

PCR can be carried out, e.g., by use of a Perkin-Elmer Cetus thermal cycler and Taq polymerase (Gene Amp™). One can choose to synthesize several different degenerate primers, for use in the PCR reactions. It is also possible to vary the stringency of annealing conditions used in priming the PCR reactions, to allow for greater or lesser degrees of nucleotide sequence similarity between the degenerate primers and the corresponding sequences in *M. catarrhalis* DNA. After successful amplification of a segment of the sequence encoding the OMP21 polypeptide, that segment may be molecularly cloned and sequenced, and utilized as a probe to isolate a complete genomic clone. This, in turn, will permit the determination of the gene's complete nucleotide sequence, the analysis of its expression, and the production of its protein product for functional analysis, as described infra.

Once an OMP21 polypeptide coding sequence has been isolated from one *M. catarrhalis* strain or cultivar, it is possible to use the same approach to isolate OMP21 polypeptide coding sequences from other *M. catarrhalis* strains and cultivars. It will be recognized by those skilled in the art that the DNA or RNA sequence encoding OMP21 polypeptide (or fragments thereof) of the invention can be used to obtain other DNA or RNA sequences that hybridize with it under conditions of moderate to high stringency, using general techniques known in the art, and as discussed above.

Hybridization with an OMP21 sequence from one *M. catarrhalis* strain or cultivar under high stringency conditions will identify the corresponding sequence from other strains and cultivars. High stringency conditions vary with probe length and base composition. The formula for determining such conditions are well known in the art. See Sambrook et al., 1989, Molecular Cloning, A Laboratory Manual, Cold Spring Harbor Press, NY, Chapter 11. As used herein high stringency hybridization conditions as applied to probes of greater than 300 bases in length involve a final wash in 0.1× SSC/0.1% SDS at 68° C. for at least 1 hour (Ausubel, et al., Eds., 1989, Current Protocols in Molecular Biology, Vol. I, Greene Publishing Associates, Inc. and John Wiley & Sons, Inc., New York, at page 2.10.3). In particular embodiments, the high stringency wash in hybridization is 2×SSC, 1% SDS at 50° C. for about 20 to about 30 minutes.

One skilled in the art would be able to identify complete clones of OMP21 polypeptide coding sequence using approaches well known in the art. The extent of OMP21 polypeptide coding sequence contained in an isolated clone may be ascertained by sequencing the cloned insert and comparing the deduced size of the polypeptide encoded by the open reading frames (ORFs) with that of OMP21 and/or by comparing the deduced amino acid sequence with that of known amino acid sequence of purified OMP21. Where a partial clone of OMP21 polypeptide coding sequence has been isolated, complete clones may be isolated by using the insert of the partial clone as hybridization probe. Alternatively, a complete OMP21 coding sequence can be reconstructed from partial clones by aligning overlapping inserts.

Complete clones may be any that have ORFs with deduced amino acid sequence matching that of OMP21 or, where the complete amino acid sequence of the latter is not available, that of a peptide fragment of OMP21 and having a molecular weight corresponding to that of OMP21. Further, complete clones may be identified by the ability of their inserts, when placed in an expression vector, to produce a polypeptide that binds antibodies specific to the amino-terminal of OMP21 and antibodies specific to the carboxyl-terminal of OMP21.

Nucleic acid sequences encoding OMP21 may be produced by methods well known in the art. In one aspect, sequences encoding OMP21 can be derived by recombinant DNA methods in view of the teachings disclosed herein. For example, the coding sequence of OMP21 may be altered creating amino acid substitutions that will not affect the immunogenicity of the OMP21 or which may improve its immunogenicity. Various methods may be used, including but not limited to oligonucleotide directed, site specific mutagenesis. These and other techniques known in the art may be used to create, single or multiple mutations, such as replacements, insertions, deletions, and transpositions, as described in Botstein and Shortle, 1985, Science 229:1193-1210.

Further, DNA of OMP21 coding sequences may be truncated by restriction enzyme or exonuclease digestions. Heterologous coding sequence may be added to OMP21 coding sequence by ligation or PCR amplification. Moreover, DNA encoding the whole or a part of an OMP21 may be synthesized chemically or using PCR amplification based on the known or deduced amino acid sequence of OMP21 and any desired alterations to that sequence.

The identified and isolated DNA containing OMP21 coding sequence can be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as pBR322 or pUC plasmid derivatives. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved DNA may be modified by homopolymeric tailing. Recombinant molecules can be introduced into host cells via transformation, transfection, infection, electroporation, etc., so that many copies of the gene sequence are generated.

In an alternative method, the desired DNA containing OMP21 coding sequence may be identified and isolated after insertion into a suitable cloning vector in a "shot gun" approach. Enrichment for the desired sequence, for example, by size fractionation, can be done before insertion into the cloning vector.

In specific embodiments, transformation of host cells with recombinant DNA molecules that contain OMP21 coding sequence enables generation of multiple copies of such coding sequence. Thus, the coding sequence may be obtained in large quantities by growing transformants, isolating the recombinant DNA molecules from the transformants and, when necessary, retrieving the inserted coding sequence from the isolated recombinant DNA.

5.8. Recombinant Production of OMP21

OMP21 may be produced through genetic engineering techniques. In this case, OMP 21 is produced by an appropriate host cell that has been transformed by DNA that codes for the polypeptide. The nucleotide sequence encoding OMP21 can be inserted into an appropriate expression vector, i.e., a vector which contains the necessary elements for the transcription and translation of the inserted polypeptide-coding sequence. The nucleotide sequence encoding OMP21 is inserted into the vectors in a manner that it will be expressed under appropriate conditions (e.g., in proper orientation and correct reading frame and with appropriate expression sequences, including an RNA polymerase binding sequence and a ribosomal binding sequence).

A variety of host-vector systems may be utilized to express the polypeptide-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA, or cosmid DNA. Preferably, the host cell is a bacterium, and most preferably the bacterium is *E. coli, B. subtilis* or *Salmonella*.

Plasmid vectors containing replicon and control sequences which are derived from species compatible with the host cell may be used for the expression of the genes encoding the OMP21 in expression systems. Expression vectors contain all the necessary elements for the transcription and translation of the inserted protein coding sequence. The vector ordinarily carries a replication site, as well as marking sequences which are capable of providing phenotype selection in transformed cells. For example, *E. coli* may be transformed using pBR322 which contains genes for ampicillin and tetracycline resistance cells. Additional examples include, but are not limited to pTrc99A, pUC19, pUC18, pKK223-3, pEX1, pCAL, pET, pSPUTK, pTrxFus, pThioHis, pTrcHis, pTrcHis2, and pLEx. The plasmids or phage, must also contain, or be modified to contain, promoters which can be used by the host cell for expression of its own proteins.

In addition, phage vectors containing replicon and control sequences that are compatible with the host can be used as a transforming vector in connection with these hosts. For example, the phage in lambda GEM™-11 may be utilized in making recombinant phage vectors which can be used to transform host cells, such as *E. coli* LE392.

Promoters commonly used in recombinant DNA construction include the β-lactamase (penicillinase) and lactose promoter systems and other microbial promoters, such as the T7 promoter system as described in U.S. Pat. No. 4,952,496. Details concerning the nucleotide sequences of promoters are known, enabling a skilled worker to ligate them functionally with genes. The particular promoter used will generally be matter of choice depending upon the desired results. Hosts that are appropriate for expression of the OMP21 genes, fragments, analogs or variants thereof, may include *E. coli, Bacillus species, Haemophilus*, fungi, yeast, *Bordetella*, or the baculovirus expression system may be used.

The expression elements of vectors vary in their strengths and specificities. Depending on the host-vector system utilized, any one of a number of suitable transcription and translation elements may be used. In a specific embodiment, a chimeric protein comprising the OMP21 sequence and a pre and/or pro sequence of the host cell is expressed. In other specific embodiments, a chimeric protein comprising OMP21 sequence and an affinity purification peptide is expressed. In further specific embodiments, a chimeric protein comprising OMP21 and a useful immunogenic peptide or polypeptide is expressed. In preferred embodiments, expressed OMP21 contains a sequence forming either an outer surface epitope or the receptor-binding domain of native OMP21.

Any method known in the art for inserting DNA fragments into a vector may be used to construct expression vectors containing a chimeric gene consisting of appropriate transcriptional/translational control signals and the polypeptide coding sequences. These methods may include in vitro recombinant DNA and synthetic techniques and in vivo recombinants (genetic recombination). Expression of a nucleic acid sequence encoding OMP21 may be regulated by a second nucleic acid sequence so that the inserted sequence is expressed in a host transformed with the recombinant DNA molecule. For example, expression of the inserted sequence may be controlled by any promoter/enhancer element known in the art. Promoters which may be used to control expression of inserted sequences include, but are not limited to the SV40 early promoter region (Bernoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42) for expression in animal cells; the promoters of β-lactamase (Villa-Kamaroff et al., 1978, Proc. Natl. Acad. Sci. U.S.A. 75:3727-3731), tac (DeBoer et al., 1983, Proc. Natl. Acad. Sci. U.S.A. 80:21-25), $P_L$, or trc for expression in bacterial cells (see also "Useful proteins from recombinant bacteria" in Scientific American, 1980, 242:74-94); the nopaline synthetase promoter region or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115-120) for expression implant cells; promoter elements from yeast or other fungi such as the Gal4 promoter, the ADC (alcohol dehydrogenase) promoter, PGK (phosphoglycerol kinase) promoter, alkaline phosphatase promoter.

Expression vectors containing OMP21 coding sequences can be identified by three general approaches: (a) nucleic acid hybridization, (b) presence or absence of "marker" gene functions, and (c) expression of inserted sequences. In the first approach, the presence of a foreign gene inserted in an expression vector can be detected by nucleic acid hybridization using probes comprising sequences that are homologous to the inserted OMP21 coding sequence. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the OMP21 coding sequence is inserted within the marker gene sequence of the vector, recombinants containing the insert can be identified by the absence of the marker gene function. In the third approach, recombinant expression vectors can be identified by assaying the foreign gene product expressed by the recombinant. Such assays can be based, for example, on the physical or functional properties of OMP21 in in vitro assay systems, e.g., binding to an OMP21 ligand or receptor, or binding with anti-OMP21 antibodies of the invention.

Once a particular recombinant DNA molecule is identified and isolated, several methods known in the art may be used to propagate it. Once a suitable host system and growth conditions are established, recombinant expression vectors can be propagated and prepared in quantity. As explained above, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered OMP21 may be controlled. Furthermore, different host cells have characteristic and specific mechanisms for the translational and post-translational processing and modification of proteins. Appropriate cell lines or host systems can be chosen to ensure the desired modification and processing of the foreign protein expressed.

5.9. Applications

The present invention has many utilities. By way of example and not as limiting the invention, the OMP21, antibodies and nucleic acids of the invention are useful as reagents for clinical or medical diagnosis of *M. catarrhalis* infections and for scientific research on the properties of pathogenicity, virulence, and infectivity of *M. catarrhalis*, as well as host defense mechanisms. For example, DNA and RNA of the invention can be used as probes to identify the presence of *M. catarrhalis* in biological specimens by hybridization or PCR amplification. The DNA and RNA can also be used to identify other bacteria that might encode a polypeptide related to the *M. catarrhalis* OMP21.

OMP21 of the invention may be used to prepare polyclonal and monoclonal antibodies that can be used to further purify compositions containing the polypeptides of the invention by affinity chromatography. The polypeptides and peptides can also be used in standard immunoassays to screen for the presence of antibodies to *M. catarrhalis* in a sample. The cytotoxic antibodies of the invention are useful in passive immunizations against *M. catarrhalis* infections. OMP21 and nucleic acids encoding same may further be used as active ingredients in pharmaceutical compositions, including vaccines, to treat or prevent *M. catarrhalis* infections.

It is to be understood that the application of the teachings of the present invention to a specific problem or environment will be within the capabilities of one having ordinary skill in the art in light of the teachings contained herein.

The following examples are presented solely for the purpose of illustration and are not intended to limit the scope of the invention. Changes in form and substitution of equivalents are contemplated as circumstances suggest or render expedient. Although specific terms have been employed herein, such terms are intended in a descriptive sense and not for purposes of limitation.

Methods of molecular genetics, protein biochemistry and immunology used but not explicitly described in the disclosure and examples are amply reported in the scientific literature and are well within the ability of those skilled in the art.

6. EXAMPLE

Isolation and Characterization of the OMP21 Polypeptide and Gene Encoding Same

6.1. Materials and Methods 6.1.1. Detergent Extraction of OMP21

Strains of *M. catarrhalis* were each grown at 35° C. at 200 rpm in 1 liter of Mueller Hinton broth in a 4 liter flask. Outer membrane protein (OMP) preparations were isolated by treating 50 mg of cells (wet weight) with 0.67 ml of 1.5% n-octyl β-D-glucopyranoside (i.e., octyl glucoside; OG) or EmpigenBB™ (N-dodecyl-N,N-dimethyl-glycine, CalBiochem) in phosphate buffered saline (PBS; for 30 minutes at room temperature. Cells were pelleted in a microcentrifuge for 5 minutes and the supernatant was used as the detergent extract. Comparison of protein profiles of these extracts from a number of strains of *M. catarrhalis* to those of blebs (i.e., outer membrane vesicles) isolated by differential centrifugation, which are highly enriched for outer membrane proteins (OMPs) from *M. catarrhalis* (Murphy and Loeb, 1989, Microbial Pathogen. 6:159-174) indicates the detergent extracts contain predominately outer membrane proteins of *M. catarrhalis* (FIG. 1). This indicated that detergent extraction provided a more rapid procedure with a higher yield of outer membrane proteins as compared to outer membrane proteins prepared from blebs.

6.1.2. Amino Terminal Sequencing of OMP21

*M. catarrhalis* ATCC 49143 were grown in Mueller Hinton broth at 37° C., cells were harvested and suspended in PBS containing 1 mM magnesium sulfate. The suspension was sonicated and centrifuged at low speed. The supernatant was centrifuged at high speed and the pellet collected. The pellet was washed twice using a high speed centrifugation. The resuspended pellet was mixed with PAGE sample buffer containing SDS, and was incubated for 5 minutes in boiling water bath. The proteins were then resolved on a 12% PA with SDS and transferred to a PVDF membrane by electroblotting, then stained with coomassie blue R-250. The region of the membrane containing the OMP21 band was then cut out for amino-terminal sequencing.

6.1.3. Anti-OMP21 Antiserum

Antiserum to OMP21 were prepared by resolving OMP21 polypeptide from OG extracts of *M. catarrhalis* strain ATCC 49143 in a DEAE SEPHAROSE™ ion exchange chromatography column. The fraction containing OMP21 was injected into a rabbit to generate antiserum to OMP21 polypeptide. In addition, affinity purified antibody was prepared by injecting rabbits with blebs from *Moraxella catarrhalis* and purified using a cyanogen bromide activated agarose gel with immobilized OMP21. The gel was reacted with the antiserum and non-reactive antibodies and proteins were washed from the gel. Reactive antibodies were eluted from the gel using 100 mM glycine, pH 2.5. The eluted antibodies were washed with PBS and concentrated. The concentrate was further purified by reacting with OMP21-deletion mutants of *M. catarrhalis*. The antiserum was analyzed by Western blots as described in Section 6.1.4., examined for complement-mediated cytotoxic activity against *M. catarrhalis* as described in Section 7 and inhibition of nasopharyngeal binding as described in Section (infra).

6.1.4. Western Blots

*M. catarrhalis* were grown in Meuller Hinton broth for 48 hours at 35° C. in 5% $CO_2$. Cells were collected by centrifugation and outer membrane proteins were extracted with OG. Extracts were then mixed by suspending in 150 μl of PAGE sample buffer (360 mM Tris buffer [pH 8.8], containing 4% sodium dodecylsulfate and 20% glycerol), and incubating the suspension at 100° C. for 5 minutes. The solubilized cells were resolved on 4-20% gradient polyacrylamide gels as per Laemmli and the separated proteins were electrophoretically transferred to PVDF membranes at 100 V for 1.5 hours as previously described (Thebaine et al. 1979, Proc. Natl. Acad. Sci. USA 76:4350-4354) except 0.05% sodium dodecylsulfate was added to the transfer buffer to facilitate the movement of proteins from the gel. The PVDF membranes were then pretreated with 25 ml of Dulbecco's phosphate buffered saline containing 0.5% sodium casein, 0.5% bovine serum albumin and 1% goat serum. All subsequent incubations were carried out using this pretreatment buffer.

PVDF membranes were incubated with 25 ml of a 1:500 dilution of serum from a rabbit immunized with OMP21 polypeptide (as described above) for 1 hour at room temperature. PVDF membranes were then washed twice with wash buffer (20 mM Tris buffer [pH 7.5.] containing 150 mM sodium chloride and 0.05% Tween-20). PVDF membranes were incubated with 25 ml of a 1:5000 dilution of peroxidase-labeled goat anti-rabbit IgG (Jackson ImmunoResearch Laboratories, West Grove Pa. Catalog number 111-035-003) for 30 minutes at room temperature. PVDF membranes were then washed 4 times with wash buffer, and were developed with 3,3' diaminobenzidine tetrahydrochloride and urea peroxide as supplied by Sigma Chemical Co. (St. Louis, Mo. catalog number D-4418) for 4 minutes each.

6.1.5. Outer Surface Localization of OMP21

*M. catarrhalis* ATCC 49143 was grown overnight at 35-37° C. in a shaking water bath in Mueller Hinton broth. The cells were pelleted by centrifugation and then resuspended in an equal volume of Dulbecco's modification of phosphate buffered saline without calcium or magnesium. Cells were diluted in a carbonate coupling buffer (50 mM sodium bicarbonate, pH 9.6), aliquots were added to wells in a 96-well ELISA plate and stored overnight at 2-8° C. The next day, the plates were washed with PBS/Tween, incubated with a non-specific protein blocker, then washed again. The wells were then treated with 100 μl of various dilutions of anti-OMP21 antiserum, or preimmune serum from the same animal, diluted in PBS/Tween, or PBS for 2 hours, then washed 3 times with PBS/Tween. The wells were treated with 100 μl of diluted peroxidase-labeled goat antibody to mouse or rabbit IgG (Jackson ImmunoResearch Laboratories, catalog #111-035-003). The wells were incubated for 1 hour and washed 3 times in PBS/Tween. Peroxidase substrate (Kirkegaard and Perry Laboratories, Inc, Gaithersburg, Md. catalog number 50-76-00) was added to each well and the reaction incubated for 10 minutes. Substrate stop solution (Kirkegaard and Perry Laboratories, Inc, Gaithersburg, Md. catalog number 50-85-05) was added and the absorbance at 450 nm was determined for each well.

6.2. Results 6.2.1. Outer Surface Location of OMP21

Mouse anti-OMP21 antiserum was used in ELISA to determine if OMP21 polypeptide is exposed on the outer surface of *M. catarrhalis* cells. Whole *M. catarrhalis* cells reacted with anti-OMP21 antiserum whereas cells treated with preimmune serum or PBS did not. This indicates that in intact *M. catarrhalis* cells OMP21 polypeptide is reactive with anti-OMP21 antibodies. This result indicates that OMP21 polypeptide is exposed on the outer surface of *M. catarrhalis*. This finding is consistent with OMP21 polypeptide having a role in adherence or nasopharyngeal binding, and moreover, indicates that OMP21 polypeptide is useful as a vaccine.

6.2.2. Properties of OMP21 Polypeptide

OMP21 polypeptide is an outer membrane protein. This conclusion is supported by the finding that extracting *M. catarrhalis* cells with detergent solubilizes OMP21 polypeptide.

Using octyl glucoside extracts of *M. catarrhalis*, then incubating the extracts with sodium dodecyl sulfate at 100° C., and resolving the proteins on a denaturing polyacrylamide gel, we have estimated the apparent molecular weight of OMP21 polypeptide from various strains of *M. catarrhalis*, specifically those of ATCC 25238, ATCC 25240, ATCC 43617, ATCC 43618, ATCC 43627 and ATCC 43628, to range from about 16 kD to about 20 kD (FIG. 2).

OMP21 polypeptide of strain ATCC 49143 was extracted from the gel slice and was sequenced. N-terminal sequencing of the mature OMP21 polypeptide isolated from the outer membrane of ATCC 49143 yielded the following sequence:

(SEQ ID NO: 1)
AISYGNSADAQPYVGAKIGQVDAKQINGKNTAYGIYAGYN.

6.2.3. Conservation of OMP21 Polypeptide

Western blot analysis of outer membrane protein extracts of a number of *M. catarrhalis* strains and related species of bacteria showed that the anti-OMP21 antibodies bind to a polypeptide of about 16 kD to about 20 kD in many *M. catarrhalis* strains (FIG. 8). These results demonstrate the following: 1) Anti-OMP21 antibodies may be used to specifically identify and distinguish *M. catarrhalis* from related species of bacteria. See FIG. 8 in which antibodies are useful to distinguish *M. catarrhalis* from mutants that have a "knock-out" of OMP21. 2) OMP21 polypeptide may be used to generate antibodies that have diagnostic application for identification of *M. catarrhalis*. 3) Antibodies to OMP21 polypeptide of one strain (e.g., OMP21 of ATCC 49143) may be used to identify and isolate the corresponding OMP21 polypeptide of other *M. catarrhalis* strains.

7. EXAMPLE

Efficacy of OMP21 Vaccine

Cytotoxic Activity of Anti-OMP21 Antiserum

Complement-mediated cytotoxic activity of anti-OMP21 antibodies was examined to determine the vaccine potential of OMP21 polypeptide. Affinity purified antibodies to OMP21 from ATCC 49143 were prepared as described in Section 6.1.4. supra. The activities of the pre-immune serum and the anti-OMP21 antiserum in mediating complement killing of *M. catarrhalis* were examined using the "Serum Bactericidal Test" described by Zollinger et al. (Immune Responses to *Neisseria meningitis*, in Manual of Clinical Laboratory Immunology, 3rd ed., pg 347-349), except that cells of *M. catarrhalis* strains were used instead of *Neisseria meningitis* cells.

The results show that anti-OMP21 antiserum mediated complement-killing of *M. catarrhalis* ATCC 49143 but not of a deletion mutant of *M. catarrhalis* with the OMP21 gene disrupted.

8. EXAMPLE

Isolation of the omp21 Gene

8.1. Preparation of Primers

Degenerate PCR primers were designed based on the OMP21 N-terminal sequence information, including the 40 amino acid sequence depicted in SEQ ID NO:1. The sequence of these degenerate oligonucleotide primers is as follows:

(SEQ ID NO: 2)
GAY GCN CAR CCN TAY GT (128 fold degeneracy)

(SEQ ID NO: 3)
TGY TTN GCR TCN ACY TG (128 fold degeneracy)

(SEQ ID NO: 4)
GCN GAY GCN CAR CCN TAY GT (512 fold degeneracy)

(SEQ ID NO: 5)
ATN CCR TAN GCN GTR TTY TT (512 fold degeneracy)

PCR reactions (50 ul) contained 1 ug of *M. catarrhalis* genomic DNA, prepared by methods well known to those skilled in the art, the respective oligonucleotide primers at a final concentration of 0.5 uM, dNTPs at 0.2 mM, usually either 2 or 4 mM Mg++, and 2 units of Taq Polymerase. PCR was performed in an Idaho Rapidcyler using the following cycling program:

Hold 1: 94° C., 1 min;

Cycles 1-3: Denature 94° C., Anneal 55° C., Elongate 72° C. each for 30 sec for 3 cycles;

Cycle 4: Denature 94° C., Anneal 40° C., Elongate 72° C. each for 30 sec for 35 cycles;

Hold 2: 72° C., 1 min.

When used to program a PCR reaction with *M. catarrhalis* genomic DNA as a template, these primer pairs generated DNA fragments of 50 and 80 bp, respectively, as predicted. These fragments were amplified from the same gene locus as determined by using the 80 bp DNA fragment as the template in a PCR reaction with the primer pair of SEQ ID Nos: 2 and 3 to amplify the 50 bp DNA fragment described above. The 80 bp DNA fragment has the sequence depicted in SEQ ID NO:21.

PCR reactions with non-degenerate primers were performed using the same template, primer and Mg++ conditions. The specific annealing temperature of an oligonucleotide primer pair was calculated and used throughout 35 cycles of amplification. The extension times were adjusted according to the length of the amplified DNA fragment.

8.2. Suppression PCR

Suppression PCR was performed using the reagents of the Universal Genome Walker Kit and the Tth Polymerase Mix (Clontech). Nested gene-specific primers were designed based on the consensus sequence for the 80 bp amplification product from the degenerate primer PCR. Nested oligonucleotide primers (28 mer) designed for this walk were as follows:

(SEQ ID NO: 8)
CCC TAT GTT GGT GCC AAA ATT GGT CAA G (SEQ ID NO: 9)
AGA TGC AAA GCA AAT CAA CGG TAA GAA C (SEQ ID NO: 10)
GTT CTT ACC GTT GAT TTG CTT GGC ATC T (SEQ ID NO: 11)
CTT GAC CAA TTT TGG CAC CAA CAT AGG G

Initial amplifications were done with combinations of the anchor primer API from the kit and SEQ ID NOs: 8 and 10, respectively. The PCR reactions (50 ul) contained 5 ng of DNA digested to completion with a number of six base pair blunt end cutters and subsequently ligated to the genome walker adaptor. Mg++ was 1.1 mM and dNTPs were used at a concentration of 0.2 mM. The cycling conditions for the primary PCR were as follows:

Cycle 1: Denature 94° C., 2 sec, Anneal and Elongate 72° C., 3 min for 7 cycles;

Cycle 2: Denature 94° C., 2 sec. Anneal and Elongate 67° C., 3 min for 32 cycles;

Hold: 67° C., 4 min.

For the secondary PCR reaction, 1 ul of a ⅕₀ dilution of the primary PCR reaction was used as the template. Reactants and cycling parameters were as above with the exception that the nested anchor primer 2 from the kit was used in combination with the nested gene specific primers SEQ ID NOs: 9 and 11, respectively.

8.3. Isolation and Subcloning of the PCR Product

The PCR products generated with degenerate oligonucleotide primers were separated on a 3.5% NuSieve agarose gel (FMC Bioproducts) using a 20 bp DNA ladder (Invitrogen) as a size marker. Relevant DNA bands were excised from the gel and recovered on Geneclean Glassmilk (BIO 101). The same procedure was used to recover the products of the suppression PCR from a 1% agarose gel. All gel purified PCR products were ligated with EcoRV digested pBluescript II SK (20 ng) and electroporated into TOP F' E. coli competent cells. After recovery on SOC medium (BRL) for 1 hr @ 37° C., aliquots of the culture were plated on LB/x-gal/IPTG/Amp plates and grown over night at 37° C.

8.4. Identification of Recombinant Plasmids

White colonies from the transformation were picked directly into a PCR reaction that was primed with commercially available T7 and T3 promoter oligonucleotides. Insertless colonies gave rise to a 160 bp DNA amplification product, whereas plasmids with the 50 bp and 80 bp PCR amplification products yielded band of 210 and 240 bp in this assay, respectively. Several positive colonies were grown and high quality plasmid DNA was prepared by methods known to those skilled in the art (described in laboratory handbooks such as Molecular Cloning).

8.5. Sequence Analysis

The sequence of the inserts in recombinant plasmids was determined using the fluorescent dideoxy-termination method. Reactions were analyzed on a ABI Prism 310 Genetic Analyzer. The 50 and 80 bp amplification products of the degenerate oligonucleotide primers were sequenced from both strands using the T3 and T7 promoter primers. The 500 and 1000 bp DNA fragments from the suppression PCR were initially sequenced with the same primers. In order to obtain the sequence of the complete omp21 ORF, several gene specific primers were synthesized and used to corroborate the sequence. The sequence of these oligonucleotides is shown below:

```
    GCG ACA AAA CCA GCC TAG       (SEQ ID NO: 12)

GGT GTT GGT GTT GGC TTT       (SEQ ID NO: 13)

CCC CTT TAA AAC ATC GCC AC.   (SEQ ID NO: 14)
```

The nucleotide sequence of the entire omp21 gene is shown in FIG. 3 and is identified as SEQ ID NO:6. A deduced amino acid sequence of the open reading frame of OMP21 is shown FIG. 4, and is identified as SEQ ID NO:7.

9. EXAMPLE

Preparation of Recombinant OMP21

9.1. Construction of an Expression Vector

To facilitate the cloning into the expression plasmid pTrc 99A (Pharmacia), a NcoI site was introduced into the OMP21 ORF at the start methionine. This change in the DNA sequence affects the second codon of the OMP 21 ORF as well by changing lysine to glutamic acid. To make this change more conservative the second codon was mutated to encode alanine. Mutations at the 3' end of the OMP21 extended the ORF by a stretch of six histidines, followed by a translational stop and a HindIII restriction site. These changes were introduced entirely by PCR using the composite primers shown below and M. catarrhalis genomic DNA as the template.

```
                                       (SEQ ID NO: 15)
gga cgc cat ggc aAC TTT AAA AAC ACT ATT GGC AGT

ATC AGC TTC (SEQ ID NO: 16)
atc aag ctt agt gat ggt gat ggt gat gAA AAG CCA

AAT GAG CGC
```

The resulting expression construct is designated as pOMP21x. The mutations described above were verified by sequencing the modified 5' and 3' ends of the insert.

9.2. Expression of OMP21

E. coli containing the expression plasmid pOMP21x was grown in L-broth containing 100 mg/ml of ampicillin at 34° C. to an absorbance at 550 nm of 0.6, then isopropylthio β-galactosidase was added to a concentration of 1 mM. The culture was allowed to continue to grow for 3 h. The cells were collected by centrifugation at 5000 g for 10 min. The cells (1 g) were suspended to 10% (w/v) on PBS. OMP21 from these cells was prepared by detergent extract (as described in Section 6.1.2.) and SDS-PAGE as described in Section 6.1.4.

10. EXAMPLE

Verification of the omp21 Gene

10.1. Construction of an omp21 Gene-Targeting Cassette

A gene targeting cassette was assembled from two PCR amplified regions of the omp 21 gene and a Kanamycin Resistance GenBlock™ (Pharmacia). The targeting region 5' to the Kanamycin gene was amplified using the primer pair SEQ ID NO 17 and SEQ ID NO 18. These composite primers amplify a ⁻550 bp DNA fragment from genomic M. catarrhalis DNA and introduce a SmaI and a PstI restriction site, respectively, at the end of the fragment. The targeting region 3' from the Kanamycin gene was amplified in the same manner using the primers SEQ ID NO 19 and SEQ ID NO 20. These composite primers amplify a 1 kb DNA fragment that has PstI and SalI sites, respectively, at the ends. The conditions for the PCR amplification were as follows:

Hold 1: 94° C. for 30 sec;
Cycle: Denature 94° C. for 10 sec, Anneal 60° C. for 15 sec, Elongate 72° C. for 45 sec, for 35 cycles;
Hold 2: 72° C. for 1 min.

Sequence of the PCR primers (restriction sites introduced are underlined):

```
                                              (SEQ ID NO: 17)
gacggcccgggCTGGTATCAATTGGCATAGGCGGTAAGTT (SEQ ID NO: 18)
catgctgcagCTTGACCAATTTTGGCACCAACATAGGG (SEQ ID NO: 19)
cactctgcagTAGACGCCAAGCAAATCAACGGTAAGAACA (SEQ ID NO: 20)
gcatgtcgacGTAGATGAGCTACAAGGCGTGATTTGGGAT.
```

The amplified DNA fragments were digested with SmaI and PstI or PstI and SalI, respectively. The 0.5 kb SmaI/PstI DNA fragment was cloned into the plasmid pCR-Script AMP SK(+) (Stratagene) in the same cloning sites. Miniprep DNA from a recombinant carrying this insert was then restricted with PstI and SalI and ligated to the 1 kb PstI/SalI insert. A recombinant carrying both flanking regions was then linearized with Pst I and the Kanamycin cassette was inserted as a 1.2 kb PstI insert. To test for functionality the transformed bacteria were plated on Kan (50 ug/ml) LB agar. Plasmids isolated from the resulting Kanamycin-resistant colonies were analyzed for the orientation of the Kanamycin insert by restriction digestion with Cla I and Sal I. Cla I cuts once in the 5' flanking 0.5 kb fragment and asymmetrically in the Kanamycin resistance gene. The resulting plasmid targeting constructs were thus designated as pomp21 K.O. (the Kanamycin resistance gene and omp21 are transcribed in the same direction) or as pomp21 O.K. (Kanamycin and omp 21 transcription proceed towards each other).

10.2 Preparation of Competent Moraxella Catarrhalis Cells

*Moraxella catarrhalis* cells were grown to an optical density (OD600 nm) of 1, harvested by centrifugation (3000×g), and subsequently washed twice in ice-cold distilled water and once in 15% glycerol. The final cell pellet was resuspended in 1-2 ml of 15% glycerol and rapidly frozen in 100 µl aliquots on dry ice. The electrocompetent cells were stored at −80° C.

10.3. Electroporation of Competent Cells

Aliquots (50 µl) of electrocompetent cells were mixed with 1 µg of plasmid DNA, transferred to a 0.1 cm electroporation cuvette and kept on ice for 1 min. An electroporation pulse was subsequently delivered using the following settings: 1500 V., 50° F. and 150µ. The pulsed culture was immediately transferred to Mueller-Hinton medium and incubated for 6 hrs at 37° C. Aliquots of the culture were then spread on selective media plates (Mueller-Hinton with 5 µg/ml of Kanamycin) and incubated at 37° C. until colonies were clearly visible (24-36 hrs). A random sample of bacteria was picked and restreaked to obtain single colonies. Individual colonies were grown in 2 ml cultures as above and used to prepare genomic DNA for PCR analysis.

10.4. PCR Analysis of Putative OMP21 Deletion Mutants

DNA from KAN$^R$ *Moraxella catarrhalis* colonies was analyzed by PCR using the primer pair SEQ ID NO: 17 and SEQ ID NO: 18. The PCR conditions were as above with the exception that the elongation time was 2 min as was the final extension (Hold 2). These primers amplify a 1.6 kb DNA fragment from wt DNA and a 2.9 kb DNA fragment from the knock-out construct. These primers were only used for the initial screening of putative knock-outs. By nature and location of the primers, this PCR analysis could not distinguish between random or homologous integrants. Clones that scored positive in this screen were further analyzed by Southern blot.

10.5. Southern Analysis of OMP 21 Deletion Mutants

*M. catarrhalis* DNA was digested with Pst I. The digests were separated on a 0.8% TAE-agarose gel and transferred to nylon membranes using standard protocols. The blots were hybridized with a $^{32}$P labeled probe prepared from a 543 bp NotI/ClaI insert released from the plasmid pCRScript-omp21. Using this probe, a 8 kb DNA fragment is detected in PstI digests of wild-type *M. catarrhalis* DNA. The same probe detects a 4.5 kb restriction fragment in all the knock-outs. The results are shown in FIG. 6. This then constitutes proof that the gene locus has been altered by homologous recombination.

11. EXAMPLE

RFLP Analysis of omp 21

Genomic DNA from wild-type *Moraxella catarrhalis* was digested with HindIII. The digests were separated on a 0.8% TAE-agarose gel and transferred to nylon membranes using standard protocols. The blots were hybridized with a $^{32}$P labeled probe prepared from the ClaI to NotI fragment of the cloning vector which contained a sequence spanning the omp21 coding region. The high stringency wash was 2×SSC, 1% SDS at 50° C. for about 20 to about 30 minutes. A single 1.8 kb fragment was detected from all strains tested. The results are shown in FIG. 5. The uniformity of the RFLP pattern shows that OMP21 gene is highly conserved in *Moraxella catarrhalis*.

12. EXAMPLE

Generation and Reactivity of Monoclonal Anti-OMP21 Antibodies

BALB/c mice are immunized with total outer membranes from *M. catarrhalis*. Hybridomas for monoclonal antibodies are prepared by fusing the spleen cells from these mice to SP2/0 cells and selecting for successful hybrids with HAT containing media. Reactive hybridomas are screened using an ELISA containing detergent extracts of the total outer member of *M. catarrhalis* MC2926. From this screen, hybridomas with varying levels of activity in the ELISA are selected for clonal selection, the monoclonal antibodies are assayed for reactivity to purified OMP21 and total outer membranes from *M. catarrhalis* MC2926_OMP21 by ELISA.

13. EXAMPLE

Nasopharyngeal Cell Binding

The binding of *Moraxella* to the continuous cell line HEp-2 was assayed using a modification of the procedure described by Galan and Curtiss (J. E. Galan and R. Curtiss III. 1989, Proc. Natl. Acad. Sci. USA 86:6383-6387, incorporated herein by reference in its entirety). The *M. catarrhalis* strains MC2926 and MC2954 were used to assay the binding of *Moraxella* to HEp-2 cells. The MC2954 strain is an isogeneic strain to MC2926 but with the gene for OMP21 disrupted (as described in Example in Section 8 above), thereby causing the loss of the expression of the OMP21 protein.

Briefly, the strains were grown to mid-log phase in Mueller Hinton broth. Bacterial cells from the culture were then centrifuged onto the monolayer of HEp-2 cells and allowed to bind to the cells for 1 hour. Nonbound cells were removed by washing with Hanks balanced salt solution containing calcium. Adherent cells were removed with the monolayer by treatment with 0.1% sodium glycocholate in phosphate buffered saline (PBS). The number of adherent cells were enumerated by plating on Mueller Hinton agar and allowing the bacteria to grow for 24 hours. The efficiency of binding of the bacteria is expressed as a percentage of bacteria bound relative to the original number of bacteria added to the HEp-2 monolayer, and is shown in Table 1 below.

TABLE 1

Binding Efficiency Of MC2926 And The Genetic Deletion Of omp 21 (MC2954) To HEp-2 Cells

| Bacterial strain | % bound |
|---|---|
| MC2926 | 100% |
| MC2954 | 45% |

The results of the nasopharyngeal cell binding assay show that OMP21 is responsible for binding and adherence of *Moraxella catarrhalis* to nasopharyngeal cells.

14. DEPOSIT OF MICROORGANISM

*E. coli* Top10F' containing plasmid OMP21X (pOMP21X), that contains the open reading frame of the gene encoding the OMP21 of *M. catarrhalis* as are described and referred to herein was deposited on Sep. 16, 1998, with the American Type Culture Collection (ATCC) located at 10801 University Boulevard, Manassas Va., 20110-2209, USA, pursuant to the Budapest Treaty and pursuant to 37 CFR 1.808 and prior to the filing of this application and assigned accession No. 98878. Samples of the deposited materials will become available to the public upon grant of a patent based upon this United Stated patent application.

The present invention described and claimed herein is not to be limited by the scope of the microorganisms or plasmids deposited, since the deposited embodiment is intended only as an illustration of the invention. Any functionally equivalent or similar microorganisms or plasmids that encode similar or equivalent proteins or fragments or analogs thereof as described in this application are intended to be within the scope of the invention. Indeed, various modifications of the invention, in addition to those shown and described herein, will become apparent to those skilled in the art from the foregoing description and accompanying drawings. Such modifications are intended to fall within the scope of the appended claims.

Other equivalents of the present invention may be readily determined by those skilled in the art and such equivalents are intended to be included in this invention. The foregoing disclosure includes all the information deemed essential to enable those skilled in the art to practice the claimed invention without undue experimentation. Because the cited patents or publications may provide further useful information, the disclosures of any and all cited materials are hereby incorporated by reference herein in their entireties.

What is claimed is:

1. A chimeric polypeptide comprising a polypeptide consisting of (a) a peptide of 6 or more consecutive amino acid residues of SEQ ID NO: 7, which peptide specifically binds to an antibody that specifically binds to the polypeptide having amino acid sequence SEQ ID NO: 7, and (b) a heterologous polypeptide fused to the amino-terminal or carboxyl-terminal of the peptide.

2. An immunogenic composition comprising an effective amount of a chimeric polypeptide comprising a polypeptide consisting of (a) a peptide of 6 or more consecutive amino acid residues of SEQ ID NO: 7, which peptide specifically binds to an antibody that specifically binds to the polypeptide having amino acid sequence SEQ ID NO: 7, and (b) a heterologous polypeptide fused to the amino-terminal or carboxyl-terminal of the peptide.

3. The immunogenic composition of claim 2, further comprising an attenuated or inactivated cultivar of *M. catarrhalis* wherein the cultivar has been genetically manipulated to have the nucleic acid encoding OMP21 deleted and therefore non-transcribed.

4. The immunogenic composition of claim 2 further comprising (a) one or more components selected from the group consisting of lipid, carbohydrate, protein, an attenuated whole organism and/or (b) an inactivated whole organism selected from the group consisting of *Moraxella, Neisseria, Pseudomonas, Streptococcus*, and *Haemophilus*.

5. The immunogenic composition of claim 2 further comprising a component selected from the group consisting of a protein or a carbohydrate from *Moraxella, Neisseria, Pseudomonas, Streptococcus*, or *Haemophilus*.

6. The immunogenic composition of claim 2 formulated as a microparticle, capsule, or liposome preparation.

7. The immunogenic composition of claim 4, wherein the lipid is a phospholipid.

8. The immunogenic composition of claim 4, wherein the carbohydrate is a lipopolysaccharide.

9. A diagnostic kit for detecting antibodies to *M. catarrhalis* comprising an immunogenic composition an effective amount of a chimeric polypeptide comprising a polypeptide consisting of (a) a peptide of 6 or more consecutive amino acid residues of SEQ ID NO: 7, which peptide specifically binds to an antibody that specifically binds to the polypeptide having amino acid sequence SEQ ID NO: 7, and (b) a heterologous polypeptide fused to the amino-terminal or carboxyl-terminal of the peptide.

* * * * *

SEQUENCE LISTING

```
<160> NUMBER OF SEQ ID NOS: 21

<210> SEQ ID NO 1
<211> LENGTH: 40
<212> TYPE: PRT
<213> ORGANISM: Moraxella catarrhalis

<400> SEQUENCE: 1

Ala Ile Ser Tyr Gly Asn Ser Ala Asp Ala Gln Pro Tyr Val Gly Ala
 1               5                  10                  15

Lys Ile Gly Gln Val Asp Ala Lys Gln Ile Asn Gly Lys Asn Thr Ala
            20                  25                  30

Tyr Gly Ile Tyr Ala Gly Tyr Asn
        35                  40

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)
<223> OTHER INFORMATION: a, g, c, t, unknown or other
<220> FEATURE:
```

```
<221> NAME/KEY: modified_base
<222> LOCATION: (12)
<223> OTHER INFORMATION: a, g, c, t, unknown or other

<400> SEQUENCE: 2
gaygcncarc cntaygt                                                  17

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)
<223> OTHER INFORMATION: a, g, c, t, unknown or other
<220> FEATURE:
<221> NAME/KEY: modified_base
<222> LOCATION: (12)
<223> OTHER INFORMATION: a, g, c, t, unknown or other

<400> SEQUENCE: 3
tgyttngcrt cnacytg                                                  17

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)
<223> OTHER INFORMATION: a, g, c, t, unknown or other
<220> FEATURE:
<221> NAME/KEY: modified_base
<222> LOCATION: (9)
<223> OTHER INFORMATION: a, g, c, t, unknown or other
<220> FEATURE:
<221> NAME/KEY: modified_base
<222> LOCATION: (15)
<223> OTHER INFORMATION: a, g, c, t, unknown or other

<400> SEQUENCE: 4
gcngaygcnc arccntaygt                                               20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)
<223> OTHER INFORMATION: a, c, g, t, unknown or other
<220> FEATURE:
<221> NAME/KEY: modified_base
<222> LOCATION: (9)
<223> OTHER INFORMATION: a, c, g, t, unknown or other
<220> FEATURE:
<221> NAME/KEY: modified_base
<222> LOCATION: (12)
<223> OTHER INFORMATION: a, c, g, t, unknown or other

<400> SEQUENCE: 5
atnccrtang cngtrttytt                                               20
```

<210> SEQ ID NO 6
<211> LENGTH: 543
<212> TYPE: DNA
<213> ORGANISM: Moraxella catarrhalis

<400> SEQUENCE: 6

```
atgaaaactt taaaaacact attggcagta tcagcttctt cgttattggc gatgagtgct    60
aacgctgcca tcagctatgg caattctgct gatgctcaac cctatgttgg tgccaaaatt   120
ggtcaagtag acgccaagca aatcaacggt aagaacaccg cttatggtat ttatgcaggt   180
tataactttg accaaaattt tggcgtagaa cccgaatttg ttggttcaga cgccaaagaa   240
tttaatgcag gcgtgagtcc tgtaaaaggt gatgtgaagt cttttggtgc ttatggcaca   300
tatcgctata acttcatcaa taccccattt tatgccaagg gcaaattagg cattgctaag   360
actaaagtag atgttaccag ccgtaatgca actacatact caaacaaaag cgacaaaacc   420
agcctagcag gcggtgttgg tgttggcttt aaaccattag caaatgtggg cgttgaagca   480
agctacaact atctatcaga agatgccaat gcaattagtt tgggcgctca tttggctttt   540
taa                                                                 543
```

<210> SEQ ID NO 7
<211> LENGTH: 180
<212> TYPE: PRT
<213> ORGANISM: Moraxella catarrhalis

<400> SEQUENCE: 7

```
Met Lys Thr Leu Lys Thr Leu Leu Ala Val Ser Ala Ser Ser Leu Leu
  1               5                  10                  15

Ala Met Ser Ala Asn Ala Ala Ile Ser Tyr Gly Asn Ser Ala Asp Ala
             20                  25                  30

Gln Pro Tyr Val Gly Ala Lys Ile Gly Gln Val Asp Ala Lys Gln Ile
         35                  40                  45

Asn Gly Lys Asn Thr Ala Tyr Gly Ile Tyr Ala Gly Tyr Asn Phe Asp
     50                  55                  60

Gln Asn Phe Gly Val Glu Ala Glu Phe Val Gly Ser Asp Ala Lys Glu
 65                  70                  75                  80

Phe Asn Ala Gly Val Ser Pro Val Lys Gly Asp Val Lys Ser Phe Gly
                 85                  90                  95

Ala Tyr Gly Thr Tyr Arg Tyr Asn Phe Ile Asn Thr Pro Phe Tyr Ala
            100                 105                 110

Lys Gly Lys Leu Gly Ile Ala Lys Thr Lys Val Asp Val Thr Ser Arg
        115                 120                 125

Asn Ala Thr Thr Tyr Ser Asn Lys Ser Asp Lys Thr Ser Leu Ala Gly
    130                 135                 140

Gly Val Gly Val Gly Phe Lys Pro Leu Ala Asn Val Gly Val Glu Ala
145                 150                 155                 160

Ser Tyr Asn Tyr Leu Ser Glu Asp Ala Asn Ala Ile Ser Leu Gly Ala
                165                 170                 175

His Leu Ala Phe
            180
```

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 8
ccctatgttg gtgccaaaat tggtcaag                                              28

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agatgccaag caaatcaacg gtaagaac                                              28

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gttcttaccg ttgatttgct tggcatct                                              28

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cttgaccaat tttggcacca acatagggg                                             28

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcgacaaaac cagcctag                                                         18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggtgttggtg ttggctttt                                                        18

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 14
cccctttaaa acatcgccac                                                    20

<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggacgccatg gcaactttaa aaacactatt ggcagtatca gcttc                        45

<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atcaagctta gtgatggtga tggtgatgaa aagccaaatg agcgc                        45

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gacggcccgg gctggtatca attggcatag gcggtaagtt                              40

<210> SEQ ID NO 18
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
catgctgcag cttgaccaat tttggcacca acataggg                                38

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cactctgcag tagacgccaa gcaaatcaac ggtaagaaca                              40

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 20
gcatgtcgac gtagatgagc tacaaggcgt gatttgggat                          40

<210> SEQ ID NO 21
<211> LENGTH: 80
<212> TYPE: DNA
<213> ORGANISM: Artificial Sequence
<220> FEATURE:
<223> OTHER INFORMATION: Description of Artificial Sequence: Synthetic
      DNA fragment

<400> SEQUENCE: 21
gacgcscarc cstatgttgg tgccaaaatt ggtcaagtag acgccaagca aatcaacggt     60
aagaacaccg cctacggaat                                                80
```